(12) United States Patent
Tunac

(10) Patent No.: US 11,821,905 B2
(45) Date of Patent: Nov. 21, 2023

(54) BIOMARKERS OF VASCULAR DISEASE

(71) Applicant: Arterez, Inc., White Lake, MI (US)

(72) Inventor: Josefino B. Tunac, Oxford, MI (US)

(73) Assignee: ARTEREZ, INC., West Bloomfield, MI (US)

( * ) Notice: Subject to any disclaimer, the term of this patent is extended or adjusted under 35 U.S.C. 154(b) by 68 days.

(21) Appl. No.: 17/469,714

(22) Filed: Sep. 8, 2021

(65) Prior Publication Data

US 2022/0057410 A1 Feb. 24, 2022

Related U.S. Application Data

(62) Division of application No. 16/060,840, filed as application No. PCT/US2016/015015 on Jan. 27, 2016, now Pat. No. 11,143,659.

(Continued)

(51) Int. Cl.
*G01N 33/68* (2006.01)
*G01N 33/86* (2006.01)

(52) U.S. Cl.
CPC ......... *G01N 33/6893* (2013.01); *G01N 33/86* (2013.01); *G01N 2333/75* (2013.01);
(Continued)

(58) Field of Classification Search
None
See application file for complete search history.

(56) References Cited

U.S. PATENT DOCUMENTS

| | | |
|---|---|---|
| 5,281,700 A | 1/1994 | Schnitzer et al. |
| 5,453,359 A | 9/1995 | Gargan et al. |

(Continued)

FOREIGN PATENT DOCUMENTS

| | | |
|---|---|---|
| CN | 1352029 A | 6/2002 |
| CN | 102353789 A | 2/2012 |

(Continued)

OTHER PUBLICATIONS

Alexander et al. (2011) "Association between γ' fibrinogen levels and inflammation" Thromb Haemost 105:605-9 [NIH Public Access—Author Manuscript—10 pages].

(Continued)

*Primary Examiner* — Erin M. Bowers
(74) *Attorney, Agent, or Firm* — Emily M. Haliday; Weaver Austin Villeneuve & Sampson LLP

(57) ABSTRACT

A biomarker panel including a four-panel test for clotting that detects soluble fibrin (SF), thrombin-antithrombin complex (TAT), antithrombin III (ATIII), and plasminogen activator inhibitor (PAI-1). A biomarker panel including a three-panel test for glycocalyx integrity that detects syndecan-1 (SDC1), heparan sulfate (HS), and hyaluronidase (HAD). A biomarker panel including a test that detects a biomarker chosen from soluble fibrin (SF), thrombin-antithrombin complex (TAT), antithrombin III (ATIII), plasminogen activator inhibitor (PAI-1), syndecan-1 (SDC1), heparan sulfate (HS), hyaluronidase (HAD), and combinations thereof. A kit including a biomarker panel, instructions for use, materials to take and apply samples to the panel, and descriptions of biomarker levels and their meaning. Methods of detecting the presence of vascular disease, determining the stage of vascular disease, monitoring the progress of vascular disease treatments, and monitoring the efficacy of drugs during drug development.

21 Claims, 14 Drawing Sheets

| Group | Mice | Diet | Day 1 | Day 3 | Day 6 |
|---|---|---|---|---|---|
| 1 | 9 | High fat | PCB-77 | | |
| 2 | 9 | High fat | PCB-77 | | $1.5 \times 10^9$ P. gingivalis |
| 3 | 9 | High fat | $5 \times 10^9$ P. gingivalis | PCB-77 | $1.5 \times 10^9$ P. gingivalis |
| 4 | 9 | High fat | PCB-77 | PCB-77 | PCB-77 |
| 5 | 9 | High fat | | | |
| 6 | 3 | Normal | | | |

| Group | Mice | Dose of P. gingivalis |
|---|---|---|
| 1 | 4 | $5 \times 10^9$ |
| 2 | 4 | $1 \times 10^9$ |
| 3 | 4 | $1 \times 10^8$ |
| 4 | 4 | $1 \times 10^7$ |

Related U.S. Application Data

(60) Provisional application No. 62/108,146, filed on Jan. 27, 2015.

(52) U.S. Cl.
CPC ............ *G01N 2333/8128* (2013.01); *G01N 2333/8132* (2013.01); *G01N 2400/40* (2013.01)

(56) References Cited

U.S. PATENT DOCUMENTS

| | | |
|---|---|---|
| 5,811,250 A | 9/1998 | Solum et al. |
| 5,843,690 A | 12/1998 | Gargan |
| 5,922,302 A | 7/1999 | Goldenberg et al. |
| 6,156,530 A | 12/2000 | Rånby |
| 8,759,095 B2 | 6/2014 | Vink et al. |
| 9,086,412 B2 | 7/2015 | Taylor et al. |
| 11,143,659 B2 | 10/2021 | Tunac |
| 2001/0051351 A1 | 12/2001 | Racis |
| 2002/0086282 A1 | 7/2002 | Pillarisetti et al. |
| 2002/0106634 A1 | 8/2002 | Adams et al. |
| 2002/0132370 A1 | 9/2002 | Lassen et al. |
| 2002/0182587 A1 | 12/2002 | Pillarisetti |
| 2003/0003515 A1 | 1/2003 | Farrell et al. |
| 2003/0008911 A1 | 1/2003 | Evans et al. |
| 2003/0036103 A1 | 2/2003 | Pillarisetti et al. |
| 2003/0040505 A1 | 2/2003 | Fogelman et al. |
| 2003/0124536 A1 | 7/2003 | McCarthy |
| 2003/0166004 A1 | 9/2003 | Gyuris et al. |
| 2003/0199000 A1 | 10/2003 | Valkirs et al. |
| 2003/0219813 A1 | 11/2003 | Yang et al. |
| 2004/0002124 A1 | 1/2004 | Lau et al. |
| 2004/0038856 A1 | 2/2004 | Chakravarty et al. |
| 2004/0047861 A1 | 3/2004 | Kehrel et al. |
| 2004/0121343 A1 | 6/2004 | Buechler et al. |
| 2004/0142334 A1 | 7/2004 | Schacht |
| 2004/0142496 A1 | 7/2004 | Nicholson et al. |
| 2004/0203083 A1 | 10/2004 | Buechler et al. |
| 2004/0213789 A1 | 10/2004 | Yacoby-Zeevi et al. |
| 2004/0215087 A1 | 10/2004 | Genero et al. |
| 2004/0253637 A1 | 12/2004 | Buechler et al. |
| 2005/0032140 A1 | 2/2005 | Kurosawa et al. |
| 2005/0065184 A1 | 3/2005 | Wolf |
| 2005/0069969 A1 | 3/2005 | Berg et al. |
| 2005/0089914 A1 | 4/2005 | Yamasaki |
| 2005/0107601 A1 | 5/2005 | Loeb |
| 2005/0181386 A1 | 8/2005 | Diamond et al. |
| 2005/0250156 A1 | 11/2005 | Shebuski et al. |
| 2006/0003338 A1 | 1/2006 | Deng et al. |
| 2006/0039863 A1 | 2/2006 | Schirner et al. |
| 2006/0105323 A1 | 5/2006 | Whitelaw et al. |
| 2006/0269552 A1 | 11/2006 | Yacoby-Zeevi et al. |
| 2006/0275214 A1 | 12/2006 | Gregor et al. |
| 2006/0286681 A1 | 12/2006 | Lehmann et al. |
| 2007/0065879 A1 | 3/2007 | Conover et al. |
| 2007/0134814 A1 | 6/2007 | Kajander et al. |
| 2007/0141055 A1 | 6/2007 | Kajander et al. |
| 2007/0141632 A1 | 6/2007 | Xu et al. |
| 2007/0196926 A1 | 8/2007 | Soito et al. |
| 2007/0213255 A1 | 9/2007 | Hastings et al. |
| 2007/0225222 A1 | 9/2007 | Chiquet-Ehrismann et al. |
| 2007/0225261 A1 | 9/2007 | Miller et al. |
| 2007/0239483 A1 | 10/2007 | Chandler et al. |
| 2007/0269836 A1* | 11/2007 | McPherson ........ G01N 33/6893 435/7.1 |
| 2008/0009684 A1 | 1/2008 | Corsetti et al. |
| 2008/0010024 A1 | 1/2008 | Diamond |
| 2008/0057516 A1 | 3/2008 | Saarma et al. |
| 2008/0121025 A1 | 5/2008 | Okazaki |
| 2008/0124277 A1 | 5/2008 | Arap et al. |
| 2008/0160007 A1 | 7/2008 | Powell |
| 2008/0300797 A1 | 12/2008 | Tabibiazar et al. |
| 2008/0300798 A1 | 12/2008 | McDevitt et al. |
| 2008/0311606 A1 | 12/2008 | Chapman-Montgomery et al. |
| 2009/0011055 A1 | 1/2009 | Lawrence et al. |
| 2009/0054256 A1 | 2/2009 | Dogulu et al. |
| 2009/0104121 A1 | 4/2009 | Madasamy |
| 2009/0155827 A1 | 6/2009 | Zeiher et al. |
| 2009/0197344 A1 | 8/2009 | Villard-Saussine et al. |
| 2009/0215042 A1 | 8/2009 | Sella-Tavor et al. |
| 2009/0246810 A1 | 10/2009 | Maier et al. |
| 2009/0263827 A1 | 10/2009 | Johansen |
| 2010/0028335 A1 | 2/2010 | Lu et al. |
| 2010/0068705 A1 | 3/2010 | Helgadottir et al. |
| 2010/0105046 A1 | 4/2010 | Epstein et al. |
| 2010/0112587 A1 | 5/2010 | Hare et al. |
| 2010/0130403 A1 | 5/2010 | Pfuetzner et al. |
| 2010/0158896 A1 | 6/2010 | Brown et al. |
| 2010/0159474 A1 | 6/2010 | Bergmann et al. |
| 2010/0209350 A1 | 8/2010 | Pfuetzner et al. |
| 2010/0233085 A1 | 9/2010 | Kwon et al. |
| 2010/0248288 A1 | 9/2010 | Hess et al. |
| 2010/0249064 A1 | 9/2010 | Singleton et al. |
| 2010/0261284 A1 | 10/2010 | Spanuth |
| 2010/0267025 A1 | 10/2010 | Young |
| 2010/0267062 A1 | 10/2010 | Frey et al. |
| 2010/0286053 A1 | 11/2010 | Kuan et al. |
| 2010/0291614 A1 | 11/2010 | Nitz et al. |
| 2010/0304424 A1 | 12/2010 | Vink et al. |
| 2010/0310646 A1 | 12/2010 | Oxvig et al. |
| 2011/0003297 A1 | 1/2011 | Liew |
| 2011/0008346 A1 | 1/2011 | Duckers |
| 2011/0070601 A1 | 3/2011 | Kastrup |
| 2011/0076692 A1 | 3/2011 | Sista et al. |
| 2011/0083199 A1 | 4/2011 | Essers et al. |
| 2011/0104735 A1 | 5/2011 | Buehrer et al. |
| 2011/0107821 A1 | 5/2011 | Hess et al. |
| 2011/0111527 A1 | 5/2011 | Hess et al. |
| 2011/0117589 A1 | 5/2011 | Bergmann et al. |
| 2011/0136157 A1 | 6/2011 | Cooper |
| 2011/0137131 A1 | 6/2011 | Adourian et al. |
| 2011/0177610 A1 | 7/2011 | Matsuo et al. |
| 2011/0229911 A1 | 9/2011 | Bergmann et al. |
| 2011/0262444 A1 | 10/2011 | Kim |
| 2011/0274749 A1 | 11/2011 | Gaillard et al. |
| 2012/0003751 A1 | 1/2012 | Bergmann et al. |
| 2012/0028880 A1 | 2/2012 | Pasqualini et al. |
| 2012/0149131 A1 | 6/2012 | Struck et al. |
| 2012/0164669 A1 | 6/2012 | Hess et al. |
| 2012/0208715 A1 | 8/2012 | McDevitt et al. |
| 2012/0208762 A1 | 8/2012 | Dudley |
| 2012/0219943 A1 | 8/2012 | Ky et al. |
| 2012/0231472 A1 | 9/2012 | Anderberg et al. |
| 2012/0264636 A1 | 10/2012 | Holm et al. |
| 2013/0004487 A1 | 1/2013 | Zeiher et al. |
| 2013/0052637 A1 | 2/2013 | Kovar et al. |
| 2013/0137632 A1 | 5/2013 | Pfuetzner et al. |
| 2013/0164284 A1 | 6/2013 | Lu et al. |
| 2013/0171649 A1 | 7/2013 | Mayr |
| 2013/0190197 A1 | 7/2013 | Liew |
| 2013/0210041 A1 | 8/2013 | Anderberg et al. |
| 2013/0261177 A1 | 10/2013 | Johansson et al. |
| 2013/0273096 A1 | 10/2013 | Daniels |
| 2013/0302841 A1 | 11/2013 | Struck et al. |
| 2014/0024551 A1 | 1/2014 | Mayr |
| 2014/0044797 A1 | 2/2014 | Johansson et al. |
| 2014/0065648 A1 | 3/2014 | Wienhues-Thelen et al. |
| 2014/0100128 A1 | 4/2014 | Narain et al. |
| 2014/0141986 A1 | 5/2014 | Spetzler et al. |
| 2014/0147867 A1 | 5/2014 | Arnold et al. |
| 2014/0206698 A1 | 7/2014 | Dudley |
| 2014/0271464 A1 | 9/2014 | Garcia-Martinez et al. |
| 2014/0315752 A1 | 10/2014 | Anderberg et al. |
| 2014/0324460 A1 | 10/2014 | Caffrey et al. |
| 2014/0357505 A1 | 12/2014 | Mohler, III et al. |
| 2015/0010929 A1 | 1/2015 | Anderberg et al. |
| 2015/0057325 A1 | 2/2015 | Johansson et al. |
| 2015/0064139 A1 | 3/2015 | Shoemaker et al. |
| 2015/0079615 A1 | 3/2015 | Wienhues-Thelen et al. |
| 2015/0087727 A1 | 3/2015 | Bergmann et al. |
| 2015/0099311 A1 | 4/2015 | Holmes et al. |
| 2015/0160229 A1 | 6/2015 | Schaal et al. |
| 2015/0175979 A1 | 6/2015 | Bottini et al. |

(56) References Cited

U.S. PATENT DOCUMENTS

| | | |
|---|---|---|
| 2015/0268251 A1 | 9/2015 | Zaugg et al. |
| 2015/0308939 A1 | 10/2015 | Oberleithner |
| 2015/0346217 A1 | 12/2015 | Spanuth |
| 2015/0376704 A1 | 12/2015 | Harrington et al. |
| 2016/0084849 A1 | 3/2016 | Chojkier et al. |
| 2016/0109464 A1 | 4/2016 | Horsch et al. |
| 2016/0121023 A1 | 5/2016 | Edelman et al. |
| 2016/0169911 A1 | 6/2016 | Block et al. |
| 2016/0252526 A1 | 9/2016 | Bergmann et al. |
| 2016/0282362 A1 | 9/2016 | Karsdal et al. |
| 2016/0320411 A1 | 11/2016 | Struck et al. |
| 2016/0320416 A1 | 11/2016 | Pugia et al. |
| 2016/0327548 A1 | 11/2016 | Crawford et al. |
| 2017/0010280 A1 | 1/2017 | Tanaka et al. |
| 2017/0010283 A1 | 1/2017 | Karl et al. |
| 2017/0138961 A1 | 5/2017 | Hess et al. |
| 2017/0218091 A1 | 8/2017 | Ambrosi |
| 2017/0227552 A1 | 8/2017 | Latini et al. |
| 2017/0234853 A1 | 8/2017 | Contant et al. |
| 2017/0269106 A1 | 9/2017 | Everett et al. |
| 2017/0304389 A1 | 10/2017 | Mann |
| 2018/0000972 A1 | 1/2018 | Lee |
| 2018/0003685 A1 | 1/2018 | Cummings et al. |
| 2018/0003725 A1 | 1/2018 | Kline |
| 2018/0031483 A1 | 2/2018 | Singamaneni et al. |
| 2018/0036285 A1 | 2/2018 | Tunac et al. |
| 2018/0088131 A1 | 3/2018 | Ostrowski et al. |
| 2018/0100862 A1 | 4/2018 | Goix et al. |
| 2018/0291374 A1 | 10/2018 | Bloch et al. |
| 2018/0292414 A1 | 10/2018 | Amir et al. |
| 2018/0298341 A1 | 10/2018 | Elliman |
| 2018/0364257 A1 | 12/2018 | Tunac |
| 2019/0010223 A1 | 1/2019 | Smith |
| 2019/0112582 A1 | 4/2019 | Redondo Moya et al. |
| 2019/0224135 A1 | 7/2019 | Struck et al. |
| 2019/0227074 A1 | 7/2019 | Denk et al. |
| 2019/0227081 A1 | 7/2019 | Struck et al. |
| 2019/0250126 A1 | 8/2019 | Hall et al. |
| 2019/0369114 A1 | 12/2019 | Van Eyk et al. |
| 2020/0003759 A1 | 1/2020 | Vath et al. |
| 2020/0018747 A1 | 1/2020 | King et al. |
| 2020/0041496 A1 | 2/2020 | Kershner et al. |
| 2020/0049721 A1 | 2/2020 | Bergmann |
| 2020/0166523 A1 | 5/2020 | Gill et al. |
| 2020/0199510 A1 | 6/2020 | Luo et al. |
| 2020/0241019 A1 | 7/2020 | Kim |
| 2020/0271670 A1 | 8/2020 | Block et al. |

FOREIGN PATENT DOCUMENTS

| | | |
|---|---|---|
| CN | 102863530 A | 1/2013 |
| CN | 104914247 A | 9/2015 |
| CN | 109055368 A | 12/2018 |
| DE | 20220351 U1 | 8/2003 |
| DE | 10247356 A1 | 4/2004 |
| DE | 10316059 A1 | 11/2004 |
| EP | 2439535 A1 | 4/2012 |
| EP | 2597467 A1 | 5/2013 |
| JP | 2003227837 A | 8/2003 |
| JP | 2008188016 A | 8/2008 |
| JP | 2011038858 A | 2/2011 |
| JP | 2015047141 A | 3/2015 |
| JP | 2018021797 A | 2/2018 |
| JP | 2019158753 A | 9/2019 |
| KR | 20060105654 A | 10/2006 |
| KR | 20090048056 A | 5/2009 |
| KR | 20180055319 A | 5/2018 |
| RU | 2154977 C1 | 8/2000 |
| RU | 2158532 C1 | 11/2000 |
| RU | 2248744 C1 | 3/2005 |
| RU | 2533836 C1 | 11/2014 |
| RU | 2550722 C1 | 5/2015 |
| RU | 2557916 C1 | 7/2015 |
| RU | 2592237 C1 | 7/2016 |
| RU | 2617418 C1 | 4/2017 |
| RU | 2720672 C1 | 5/2020 |
| UA | 57001 U | 2/2011 |
| UA | 60581 U | 6/2011 |
| UA | 92604 U | 8/2014 |
| WO | WO-9310261 A1 | 5/1993 |
| WO | WO-9810293 A1 | 3/1998 |
| WO | WO-9826092 A1 | 6/1998 |
| WO | WO-9826292 A1 | 6/1998 |
| WO | WO-9918442 A1 | 4/1999 |
| WO | WO-9948916 A2 | 9/1999 |
| WO | WO-9964627 A2 | 12/1999 |
| WO | WO-0050639 A2 | 8/2000 |
| WO | WO-0111064 A2 | 2/2001 |
| WO | WO-0123426 A2 | 4/2001 |
| WO | WO-0173445 A2 | 10/2001 |
| WO | WO-0202593 A2 | 1/2002 |
| WO | WO-2004001421 A2 | 12/2003 |
| WO | WO-2006052924 A2 | 5/2006 |
| WO | WO-2006115047 A1 | 11/2006 |
| WO | WO-2007070021 A1 | 6/2007 |
| WO | WO-2008009869 A1 | 1/2008 |
| WO | WO-2008040328 A2 | 4/2008 |
| WO | WO-2009033095 A2 | 3/2009 |
| WO | WO-2009058168 A1 | 5/2009 |
| WO | WO-2009100907 A1 | 8/2009 |
| WO | WO-2009128917 A2 | 10/2009 |
| WO | WO-2010018203 A1 | 2/2010 |
| WO | WO-2010026272 A1 | 3/2010 |
| WO | WO-2010047767 A2 | 4/2010 |
| WO | WO-2010054810 A1 | 5/2010 |
| WO | WO-2010133173 A1 | 11/2010 |
| WO | WO-2012009547 A2 | 1/2012 |
| WO | WO-2012020045 A1 | 2/2012 |
| WO | WO-2012066140 A1 | 5/2012 |
| WO | WO-2013045570 A1 | 4/2013 |
| WO | WO-2013188787 A1 | 12/2013 |
| WO | WO-2015073709 A2 | 5/2015 |
| WO | WO-2015110957 A2 | 7/2015 |
| WO | WO-2016123163 A2 | 8/2016 |
| WO | WO-2016126662 A1 | 8/2016 |
| WO | WO-2016130802 A1 | 8/2016 |
| WO | WO-2017136652 A1 | 8/2017 |
| WO | WO-2018042072 A1 | 3/2018 |
| WO | WO-2018136825 A1 | 7/2018 |
| WO | WO-2018178386 A1 | 10/2018 |
| WO | WO-2018208846 A1 | 11/2018 |
| WO | WO-2019183671 A1 | 10/2019 |
| WO | WO-2020018005 A1 | 1/2020 |
| WO | WO-2020053355 A2 | 3/2020 |
| WO | WO-2020074777 A1 | 4/2020 |
| WO | WO-2020081866 A1 | 4/2020 |
| WO | WO-2020115288 A1 | 6/2020 |
| WO | WO-2020146263 A1 | 7/2020 |
| WO | WO-2020148769 A1 | 7/2020 |
| WO | WO-2020167735 A1 | 8/2020 |
| WO | WO-2021062298 A1 | 4/2021 |

OTHER PUBLICATIONS

Allender et al. (2008) "Patterns of coronary heart disease mortality over the 20th century in England and Wales: Possible plateaus in the rate of decline" BMC Public Health 8:148 (12 pages).

Appiah et al. (2015) "Association of Plasma γ' Fibrinogen With Incident Cardiovascular Disease The Atherosclerosis Risk in Communities (ARIC) Study" Arterioscler Thromb Vasc Biol. 35(12):2700-2706.

Canadian Office Action dated Jan. 6, 2022 issued in CA 3,012,985.

Co-pending U.S. Appl. No. 17/762,703, filed Mar. 22, 2022.

Cosin-Sales et al. (2004) "Pregnancy-Associated Plasma Protein A and Its Endogenous Inhibitor, the Proform of Eosinophil Major Basic Protein (proMBP), Are Related to Complex Stenosis Morphology in Patients With Stable Angina Pectoris" Circulation 109(14):1724-1728.

Danesh et al. (2005) "Plasma Fibrinogen Level and the Risk of Major Cardiovascular Diseases and Nonvascular Mortality An Individual Participant Meta-analysis" JAMA 294(14):1799-1809.

International Preliminary Report on Patentability dated Apr. 7, 2022, in Application No. PCT/US2020/052912.

(56) References Cited

OTHER PUBLICATIONS

Kalousová et al. (2014) "Pregnancy-associated plasma protein A associates with cardiovascular events in diabetic hemodialysis patients." Atherosclerosis 236(2):263-269.

Lindahl, Bertil (2013) "The Story of Growth Differentiation Factor 15: Another Piece of the Puzzle" Clinical Chemistry 59(11): 1550-1552.

Lovely (2010) "γ' Fibrinogen: Evaluation of a New Assay for Study of Associations with Cardiovascular Disease" Clin Chem 2010; 56(5):781-8.

Lovely et al. (2011) "Assessment of Genetic Determinants of the Association of γ' Fibrinogen in Relation to Cardiovascular Disease" Arterioscler Thromb Vasc Biol. 31(10): 2345-2352.

Mannila et al. (2007) "Elevated plasma fibrinogen gamma' concentration is associated with myocardial infarction: effects of variation in fibrinogen genes and environmental factors" J Thromb Haemost 5(4):766-73 doi: 10.1111/j.1538-7836.2007.02406.x. Epub Jan. 22, 2007.

Meh et al. (1996) "Identification and Characterization of the Thrombin Binding Sites on Fibrin" J Biol Chem 271(38):23121-23125.

Mueller et al. (2006) "Increased pregnancy-associated plasma protein-A as a marker for peripheral atherosclerosis: results from the Linz Peripheral Arterial Disease Study" Clin Chem 52(6):1096-1103.

Papageorgiou et al. (2017) "Coronary Artery Atherosclerosis in Hypertensive Patients: The Role of Fibrinogen Genetic Variability" Rev Esp Cardiol. 70:34-41.

Parveen et al. (2015) "Pregnancy Associated Plasma Protein-A (PAPP-A) Levels in Acute Coronary Syndrome: A Case Control Study in a Tertiary Care Centre" Indian J Clin Biochem. 30(2): 150-154.

PCT International Preliminary Report on Patentability and Written Opinion dated Aug. 1, 2017 issued in PCT/US2016/015015.

PCT International Search Report and Written Opinion dated Feb. 24, 2021 issued in PCT/US2020/052912.

PCT International Search Report and Written Opinion dated Jul. 18, 2016 issued in PCT/US2016/015015.

Robbers et al. (2013) "Magnetic resonance imaging-defined areas of microvascular obstruction after acute myocardial infarction represent microvascular destruction and haemorrhage" Eur Heart J. 34:2346-2353.

Rohatgi et al. (2012) "Association of Growth Differentiation Factor-15 with Coronary Atherosclerosis and Mortality in a Young, Multiethnic Population: Observations from the Dallas Heart Study" Clinical Chemistry 58(1):172-182.

Tunac (2021) "Curative and Preventive Treatment for Cardiovascular Disease (CVD) Targeting Multiple Etiology" Cardiology and Cardiovascular Research 5(2): 103-125.

U.S. Notice of Allowance dated Feb. 18, 2021 issued in U.S. Appl. No. 16/060,840.

U.S. Notice of Allowance dated Jun. 9, 2021 issued in U.S. Appl. No. 16/060,840.

U.S. Office Action dated May 18, 2020 issued in U.S. Appl. No. 16/060,840.

Van den Herik et al. (2011) "γ'/total fibrinogen ratio is associated with short-term outcome in ischaemic stroke" Thromb Haemost 105(3):430-4; doi: 10.1160/TH10-09-0569. Epub Dec. 6, 2010.

Van den Herik et al. (2012) "Fibrinogenγ'levels in patients with intracerebral hemorrhage" Thrombosis Research 129(6): 807-809.

Wallentin et al. (2014) "Growth Differentiation Factor 15, a Marker of Oxidative Stress and Inflammation, for Risk Assessment in Patients With Atrial Fibrillation" Circulation 130:1847-1858.

Wiklund et al. (2010) "Macrophage inhibitory cytokine-1 (MIC-1/GDF15): a new marker of all-cause mortality" Aging Cell 9: 1057-1064.

Wollert et al. (2017) "Growth Differentiation Factor 15 as a Biomarker in Cardiovascular Disease" Clinical Chemistry 63(1): 140-151.

Wu et al. (2016) "Level of Pregnancy-associated Plasma Protein-A Correlates With Coronary Thin-cap Fibroatheroma Burden in Patients With Coronary Artery Disease: Novel Findings From 3-Vessel Virtual Histology Intravascular Ultrasound Assessment" Medicine (Baltimore) 95(3): e2563 (7 pages).

Zengin et al. (2015) "The utility of pregnancy-associated plasma protein A for determination of prognosis in a cohort of patients with coronary artery disease" Biomark Med. 9:731-741 ((Epub ahead of print—10.2217/BMM.15.41 ISSN 1752-0363 11 pages).

Zimmers et al. (2005) "Growth differentiation factor-15/macrophage inhibitory cytokine-1 induction after kidney and lung injury" Shock 23(6): 543-8.

\* cited by examiner

| Group | Mice | Diet | Day 1 | Day 3 | Day 6 |
|---|---|---|---|---|---|
| 1 | 9 | High fat | PCB-77 | | |
| 2 | 9 | High fat | PCB-77 | | $1.5 \times 10^9$ P. gingivalis |
| 3 | 9 | High fat | $5 \times 10^9$ P. gingivalis | PCB-77 | $1.5 \times 10^9$ P. gingivalis |
| 4 | 9 | High fat | PCB-77 | PCB-77 | PCB-77 |
| 5 | 9 | High fat | | | |
| 6 | 3 | Normal | | | |

FIGURE 1A

| Group | Mice | Dose of P. gingivalis |
|---|---|---|
| 1 | 4 | $5 \times 10^9$ |
| 2 | 4 | $1 \times 10^9$ |
| 3 | 4 | $1 \times 10^8$ |
| 4 | 4 | $1 \times 10^7$ |

FIGURE 1B

Group 3 (bacteria + PCB77)  Group 4 (3x PCB 77)

Created a CVD model in mouse
Proprietary: Treatment with high fat diet, PCB & *P. gingivalis*

(brachiocephalic artery X-section)

Plaque (brachiocephalic artery X-section)

Plaque no plaque
(control: normal diet)

First time regular mouse produced plaques

FIGURE 14A-C

BIOMARKERS OF VASCULAR DISEASE

CROSS-REFERENCE TO RELATED APPLICATIONS

This application is a divisional of U.S. Ser. No. 16/060,840, filed on Jun. 8, 2018, U.S. Pat. No. 11,143,659, which is a 371 US National Phase of PCT/US2016/015015, filed Jan. 27, 2016, which claims benefit of and priority to U.S. Ser. No. 62/108,146, filed on Jan. 27, 2015, all of which are incorporated herein by reference in their entireties for all purposes.

BACKGROUND OF THE INVENTION

1. Technical Field

The present invention relates to biomarkers of vascular diseases or thromboembolism. More specifically, the present invention relates to panels of biomarkers that can detect the health status of blood vessels in the general population and in vascular diseases or thromboembolism.

2. Background Art

Chronic diseases are the leading cause of morbidity with thromboembolic diseases on top of the list. Thromboembolic disease is a blood vessel or vascular abnormality common to both arteries and veins. It involves formation of a blood clot, which can subsequently dislodge to form a thrombus or embolus that flows downstream in the blood vessel tree and impairs blood flow: a process called thrombosis. Thromboembolic disease is the leading cause of morbidity and mortality in the developed world with arterial thromboses being the most common underlying cause of coronary heart disease (CHD), acute myocardial infarction (MI), stroke, hypertension, atrial fibrillation, congestive heart failure (CHF), congenital heart condition, and peripheral arterial disease (PAD); and, venous thromboses, which include chronic venous insufficiency (CVI), deep venous thrombosis (DVT) affecting approximately two million Americans annually, and pulmonary embolism (PE) accounting for 60,000 annual deaths in the United States.

Current medical textbooks consider these vascular diseases as separate and different etiologies with treatment options including the cholesterol-lowering statins, anti-hypertensives, and anticoagulants. However, despite decades of statin and anti-hypertensive therapies, vascular diseases continue to be leading killers because these drugs are not addressing the root cause of thromboembolism. Advances in biochemistry now point to clot formation as common to the pathology of thromboembolism and the risk factors for clot formation include abnormalities in the blood vessel wall, blood flow dynamics, and blood constituents.

Blood clots or thrombosis is the cause of death in various vascular diseases. To understand the etiology of clot formation, one must look at blood circulation: an average human has 60-100,000 miles of blood vessels consisting of straight and bifurcated segments. The dynamics of blood flow through these vessels is unimpeded in the straight segments but slows down at bends or bifurcations forming a 'whirlpool' flow. Whirlpool blood flow alone could cause clot formation where overcrowding produce fibrinogen, which binds to the sialic acid on the surface of red blood cells (RBC) making them stick together and acquire a 'Roleaux' formation (stacking due to flat RBC surface). This Roleaux formation subsequently gets trapped by fibrin along with white blood cells and platelets to form native clots without vessel wall injury.

Conditions that increase blood viscosity further slow down blood flow to stagnation. Thus, excessive consumption of fats contributes to increased blood viscosity. Fats or triglycerides (TG) in the diet are packaged by the liver in very low density lipoprotein (VLDL—55% TG: 9% C) for delivery to muscles as energy source. Excess dietary fat means an increased VLDL level, causing hypertriglyceridemia if fat lingers or stays in the blood stream for an extended period; or obesity after VLDL unloads its fat cargo to adipocytes. Once TG is released from VLDL, the package is reduced and becomes LDL (7% TG: 50% C), which is the source of cholesterol for the body's need; excess LDL goes back to liver for recycling or for bile.

Stagnant blood flow concentrates blood contaminants (bacterial infections, pollutants, etc.), which attracts monocytes and white blood cells (WBC), subsequently provoking an inflammatory response with the release of inflammatory cytokines and free radicals or reactive oxygen species (ROS). Over time, chronic inflammation disrupts the protective endothelial glycocalyx lining, and creates 'gaps' and osmotic imbalance in the blood vessel resulting in edema and infiltration of blood debris, e.g., dead cells, chemicals, calcium, etc.

Moreover, the denuded endothelium produces a sticky or adhesive material called e-selectin, causing activated macrophages to accumulate to form sticky 'foam cell', which matures into plaque. The processes leading to plaque build-up or atheroma (atherosclerosis) generally begin in the early years of life, as young as 5 years old, but the symptoms generally do not become apparent until after the age of 40 years.

More importantly, the endothelial glycocalyx offers a 'nest' for protective enzymes including anticoagulant antithrombin (AT-III), anti-oxidant (SOD), and anti-high blood viscosity lipoprotein lipase (LpL). Thus, the loss of endothelial glycocalyx results in a build up of fibrin, a suppression of fibrinolysis and the promotion of clot formation. Further inflammation predisposes the plaque to rupture, and ruptured plaque triggers clots formation: this clot can be exacerbated by the seed clot formed by Roleaux cells thus becoming a significant thrombus. Loose thrombi can wedge on a rigid vessel narrowed by plaque, particularly in individuals who already have atherosclerosis, causing a stroke (clogged artery to the brain), heart attack (clogged artery to the heart), or PAD (clogged artery to the arms or legs).

Meanwhile, the straight vessel segment with high blood flow has high shear stress, which is important in maintaining a thick protective endothelial glycocalyx layer. The venous system returns 'used' blood to the heart by means of the skeletal pump. The mechanism involves the contraction-relaxation motion of muscles surrounding the veins (relaxation, draws blood from superficial veins; contraction, propels blood to heart) pushing blood through the one-way valve system (preventing back-flow). Poor muscle contraction or dysfunctional valve system, due to inactivity or muscle degeneration, create stagnation and blood pooling. Concentration of blood cells is the main mechanism for clot formation, although injury to vein wall may trigger formation of blood clot as well. A loose clot becomes an embolus, which travels to the lung or heart causing a DVT.

In summary, interruptions to arterial blood flow causes blood stagnation where 'blood debris' gravitates (e.g., dead cells, 'microbial contaminants', etc.). These attract monocytes, which produce inflammatory factors (e.g., cytokines, free radicals or ROS) and eventually chronic inflammation leads to destruction of the protective endothelial glycocalyx lining. Destruction of the endothelial glycocalyx creates an osmotic imbalance causing edema and infiltration of blood components resulting in plaque formation. More importantly, loss of endothelial glycocalyx results in the shedding of built-in protective enzymes including the anti-oxidant superoxide dismutase (SOD) and catalase, anticoagulant anti-thrombin AT-III, and 'anti-viscosity' lipoprotein lipase (LpL). All these factors lead to clot formation and thrombosis. Thrombosis is typically fatal when a clot wedges on a rigid or inelastic vessel, which is narrowed by a stenotic plaque.

On the venous system, a faulty 'skeletal muscle-pump' causes stagnation or blood pooling: concentrated blood cells are trapped in fibrin and subsequently activate platelets to form clots. Loose clots become emboli that travel back to heart or lung causing deadly deep vein thrombosis (DVT). Alternatively, pooled blood attract inflammatory monocytes that disrupts the endothelial glycocalyx causing protein infiltration (extravasation), edema and varicose or spider veins.

There are several treatments available for blood clots, i.e. antithrombotics. These treatments fall into two classes, anticoagulants (that slow down clotting) and antiplatelets (that prevent clumping of platelets and clot formation). Heparin is an anticoagulant that is commonly used and administered before surgery in order to prevent clots forming. Heparin has the side effect of causing excessive bleeding and bruising and cannot be used on a long term basis. Dicumarol, and its derivative warfarin, are other anticoagulants that act as a vitamin K depleter and prevent the formation of coagulant enzymes. Fondaparinux is a synthetic anticoagulant related to low molecular weight heparin that is indicated for deep vein thrombosis and can be given daily. Bivalirudin is a synthetic anticoagulant that is a specific and reversible direct thrombin inhibitor and is indicated for patients with unstable angina undergoing percutaneous transluminal coronary angioplasty or percutaneous coronary intervention. Aspirin is an antiplatelet and widely used in low doses to reduce the risk of stroke and heart attack. Clopidogrel is an antiplatelet that irreversibly inhibits P2Y12 receptor on platelet cell membranes and can be administered along with or instead of aspirin in preventing heart disease. Dipyridamole is an antiplatelet that inhibits thrombus formation, and is also administered along with aspirin to prevent stroke and heart attack. Abciximab is another antiplatelet administered to patients undergoing percutaneous coronary intervention. While each of these antithrombotics are useful in different situations, there are still side effects and there remains a need for more effective therapeutics and diagnostics in detecting risk of blood clots.

There are several tests that can be performed to determine if an individual has vascular disease. For example, a carotid duplex is an ultrasound scan of the carotid artery that can detect stenosis or narrowing of the carotid arteries. An abdominal duplex is an ultrasound scan of the aorta that can detect abnormalities. An ankle brachial index can detect reduced blood flow in the leg. Venous ultrasound can be used to detect blood flow through vessels for detecting deep vein thrombosis and superficial vein thrombosis.

Biomarkers have been identified that can be useful for identifying individuals at risk of vascular diseases. For example, biomarkers of inflammation can indicate the presence of atherosclerosis or plaques (C-reactive protein, IL-18, IL-6). Biomarkers of lipid accumulation can indicate the presence of plaques (lipoprotein-associated phospholipase A2). Biomarkers of thrombosis can indicate the presence of plaque instability or carotid disease progression (tissue plasminogen activator (t-PA), fibrinogen, plasminogen activator inhibitor-1 (PAI-1)). However, no such biomarkers are currently in use by medical practitioners as a diagnostic tool.

U.S. Patent Application No. 2007/0269836 to McPherson, et al. discloses methods and compositions for diagnosis of venous thromboembolic disease, pulmonary embolism, and/or deep vein thrombosis, and for risk stratification in such conditions. An assay can be performed from test samples obtained from a subject to diagnose a subject, including markers used individually or in combination, such as TAT, ATIII, and PAI-1. McPherson, et al. does not disclose an assay including the marker soluble fibrin (SF).

U.S. Pat. No. 8,759,095 to Vink, et al. discloses diagnostic and therapeutic tools for diseases altering vascular function. In particular, endothelial glycocalyx perturbation can be diagnosed in samples from subjects by detecting heparan sulfate (HS) (heparan sulphate therein), hyaluronidase (HAD), and syndecan-1. Vink, et al. does not provide any particular advantages to using these particular three markers together but merely provides them as examples of relevant markers.

U.S. Patent Application No. 2013/0273096 to Daniels discloses methods of treating disorders affecting the endothelial glycocalyx. Characteristics of the endothelial glycocalyx can be determined by detecting markers in a sample from a subject, such as heparan sulfate (HS), hyaluronidase (HAD), and syndecan-1. Daniels does not provide any particular advantages to using these particular three markers together but merely provides them as examples of relevant markers.

As vascular diseases remain a large problem with society, there remains a need for a diagnostic device that can detect diseases accurately as well as indicate the stage of disease.

SUMMARY OF THE INVENTION

The present invention provides for a biomarker panel including a four-panel test for clotting that detects soluble fibrin (SF), thrombin-antithrombin complex (TAT), antithrombin III (ATIII), and plasminogen activator inhibitor (PAI-1).

The present invention provides for a biomarker panel including a three-panel test for endothelial glycocalyx integrity that detects syndecan-1 (SDC1), heparan sulfate (HS), and hyaluronidase (HAD).

The present invention provides for a biomarker panel including a test that detects a biomarker chosen from soluble fibrin (SF), thrombin-antithrombin complex (TAT), antithrombin HI (ATM), plasminogen activator inhibitor (PAI-1), syndecan-1 (SDC1), heparan sulfate (HS), hyaluronidase (HAD), and combinations thereof.

The present invention provides for a kit including a biomarker panel chosen from the four-panel test, the three-panel test, both the four-panel and three panel tests, a test that detects a biomarker chosen from soluble fibrin (SF), thrombin-antithrombin complex (TAT), antithrombin III (ATIII), plasminogen activator inhibitor (PAI-1), syndecan-1 (SDC1), heparan sulfate (HS), hyaluronidase (HAD), and combinations thereof, instructions for use, materials to take and apply samples to the panel, and descriptions of biomarker levels and their meaning.

The present invention also provides for a method of detecting the presence of vascular disease or propensity to develop vascular disease, by taking a sample, applying the sample to a biomarker panel that detects clotting, endothelial glycocalyx integrity, or combinations thereof, detecting the presence of at least one biomarker, comparing levels of the biomarker to a baseline, and determining if the individual has vascular disease or the propensity to develop vascular disease.

The present invention further provides for a method of determining the stage of vascular disease, by taking a sample, applying the sample to a biomarker panel that detects clotting, endothelial glycocalyx integrity, or combinations thereof, detecting the presence of at least one biomarker, comparing levels of the biomarker to known stage levels, and determining the stage of vascular disease.

The present invention provides for a method of monitoring the progress of vascular disease treatments by taking a sample from an individual receiving treatment for vascular disease, applying the sample to a biomarker panel chosen from a panel that detects clotting, endothelial glycocalyx integrity, or combinations thereof, detecting the presence of at least one biomarker, comparing levels of the biomarker to a baseline, and determining if the treatment is working to reverse or prevent vascular disease.

The present invention further provides for a method of monitoring the efficacy of drugs during drug development against cardiovascular diseases or other diseases involving inflammation, disruption of blood vessels, removal of plaques, or treatment of clot formation, by taking a sample from an individual receiving a drug being tested, applying the sample to a biomarker panel chosen from a panel that detects clotting, endothelial glycocalyx integrity, or combinations thereof, detecting the presence of at least one biomarker, comparing levels of the biomarker to a baseline, and determining the efficacy of the drug.

The present invention also provides for a method of detecting and monitoring vascular health by determining the status of internal vascular architecture.

DESCRIPTION OF THE DRAWINGS

Other advantages of the present invention are readily appreciated as the same becomes better understood by reference to the following detailed description when considered in connection with the accompanying drawings wherein:

FIGS. 1A and 1B are charts of experiment protocols;

DETAILED DESCRIPTION OF THE INVENTION

Figure 2A:
FIGS. 2A and 2B are photomicrographs of sections of group 3 and group 4.

Most generally, the present invention is directed to panels of biomarkers used to detect vascular diseases, and especially in detecting biomarkers that indicate abnormal biochemical elements responsible for the blood clotting cascade and biomarkers that indicate abnormal levels of enzymes and structural components of the blood vessel surface.

The term "assay" as used herein refers to a procedure that determines the amount of a particular constituent of a mixture or sample. "Assay" can interchangeably be used with the term "test" herein.

The term "biomarker" as used herein refers to a substance, such as, but not limited to, a protein, DNA sequence, RNA sequence, or other biological substance or substances that, when detected, indicates a particular healthy or unhealthy state of an individual with respect to vascular disease.

"Vascular disease", as used herein, refers to any disease affecting the circulatory system of arteries, veins, capillaries, and lymph vessels in the body. Vascular disease can include, but is not limited to, peripheral artery disease, aneurysms, renal artery disease, Raynaud's disease, Buerger's disease, peripheral venous disease, varicose veins, blood clots (thromboembolism), blood clotting disorders, lymphedema.

"Thromboembolism", as used herein, refers to a family of vascular diseases including coronary heart disease (CHD), acute myocardial infarction (MI), stroke, hypertension, atrial fibrillation, congestive heart failure (CHF), congenital heart condition, peripheral arterial disease (PAD), chronic venous insufficiency (CVI), deep venous thrombosis (DVT), and pulmonary embolism (PE).

The term "healthy" as used herein refers to a state of an individual who is free from vascular disease, is in good health, and has relatively low risk of developing vascular disease.

The term "sample" as used herein refers to a biological sample from an individual, and can be, but is not limited to, blood, plasma, urine, saliva, tears, or cerebral spinal fluid (CSF).

The present invention generally provides for a method of detecting and monitoring vascular health, by determining the status of internal vascular architecture. This status is determined by monitoring products of vascular oxidation damage and clot formation, as further described below.

Most generally, the biomarker panels include of a set of chemical, immunochemical and/or enzymatic assays or tests that can be used together for monitoring the levels of a set of biomarkers. The biomarker panels can be used to determine the presence of disease, or the propensity of an individual to develop disease. The biomarker panels can also be used to mark the progression of disease. Evaluation of different stages or components of vascular disease is important for intervention or reversal of the effects of the disease.

The biomarker panel can include a four-panel test for endothelial glycocalyx health that detects soluble fibrin (SF), thrombin-antithrombin complex (TAT), antithrombin III (ATIII), and plasminogen activator inhibitor (PAI-1).

Soluble fibrin (SF) is composed of fibrin monomer and fibrinogen derivatives, exist in the circulating blood in patients with thrombosis. Its detection and quantification are useful for obtaining information about the condition and degree of intravascular coagulation in early-stage thrombosis. The level of SF increases on coagulation, which is related to the production of blood factor VIII. Thus, factor VIII circulates in the plasma bound to von Willebrand factor (vWf). Thrombin cleaves and activates factor VIII and releases vWf. The vWf is then free to bind to ruptured endothelial cell surfaces where it activates platelet aggregation. The released FVIIIa acts as a cofactor of factor IXa to generate factor Xa. In the presence of Ca2+ and phospholipids, FX is activated to FXa by FIXa. Since FVIIIa is a cofactor to FIXa, it greatly stimulates the reaction. By using optimal amounts of Ca2+, phospholipid, and FIXa, and an excess of FX, the rate of activation of FX is linearly related to the amount of FVIII. FXa hydrolyses the chromogenic substrate S-2765 which releases the chromophoric group pNA. The color can be read at 405 nm, and generated FXa and thus the intensity of color, is proportional to the FVIII activity in the sample. A baseline level for soluble fibrin can be established that reflects the levels in a healthy individual. A healthy individual should have lower levels of SF than a diseased individual. If levels are detected with the biomarker panel that are above the baseline level, it can be determined that the individual has vascular disease or is at risk of developing vascular disease and especially thrombosis. Other levels can determine the stage or progression of vascular disease.

Another blood component that reflects blood coagulation is the formation of thrombin-antithrombin complex (TAT). TAT complex is a parameter of coagulation and fibrinolysis. Elevated concentrations have been associated with vascular disease. Antithrombin deficiency promotes clot formation in the arteries and/or veins and is associated with a high risk of thromboembolic disorders. An operational detection of TAT involves microtiter plates, which are commercially available. Thus, microtiter plates precoated with antibody specific to thrombin are commercially available. Calibrators or samples are then added to the appropriate microtiter plate wells with a biotin-conjugated polyclonal antibody preparation specific for ATIII. Next, Avidin conjugated to Horseradish Peroxidase (HRP) is added to each microplate well and incubated. Then a TMB substrate solution is added to each well. Only those wells that contain TAT, biotin-conjugated antibody and enzyme-conjugated Avidin will exhibit a change in color. The enzyme-substrate reaction is terminated by the addition of a sulfuric acid solution and the color change is measured spectrophotometrically at a wavelength of 450 nm±10 nm. The concentration of TAT in the samples is then determined by comparing the O.D. of the samples to the calibration curve. A baseline level for TAT can be established that reflects the levels in a healthy individual. A healthy individual should have lower levels of TAT than diseased individual. If levels are detected with the biomarker panel that are above the baseline level, it can be determined that the individual has vascular disease or is at risk of developing vascular disease. Other levels can determine the stage or progression of vascular disease.

Antithrombin III (AT III) is a non-vitamin K-dependent protease enzyme, which serves as a natural blood thinner and inhibits coagulation. AT III deficiency leads to increased risk of developing life-threatening clots that block blood flow. For example, deep vein thrombosis (DVT) occurs when a clot, or thrombus, develops in one of the deep veins, most common in the legs. The level of AT III is reduced when blood coagulates, which is determined by commercially available test kits. One such example of a test kit is the AssayMax Mouse AT III ELISA kit (supplier): this is designed for detection of mouse AT III in plasma, serum and cell culture supernatants. This assay employs a quantitative sandwich enzyme immunoassay technique, which measures AT III in 4 hours. Thus, a microliter plate pre-coated with polyclonal antibody specific for mouse AT III is commercially available. Mouse AT III in standards and samples is sandwiched by the immobilized antibody and biotinylated polyclonal antibody specific for mouse AT III, which is recognized by a streptavidin-peroxidase conjugate. All unbound material is then washed away and a peroxidase enzyme substrate is added. The color development is stopped and the intensity of the color is measured. A baseline level for AT III can be established that reflects the levels in a healthy individual. A healthy individual should have lower levels of AT III than a diseased individual. If levels are detected with the biomarker panel that are above the baseline level, it can be determined that the individual has vascular disease or is at risk of developing vascular disease. Other levels can determine the stage or progression of vascular disease.

Plasminogen activator inhibitor (PAI-1) is a protein, also known as endothelial plasminogen activator inhibitor or serpin E1, and is a central regulator of the blood fibrinolytic system and its production precedes thrombosis. In other words, increased PAI-1 levels increase the risk for thrombosis, whereas decreased levels cause recurrent bleeding. PAI-1 is the main inhibitor of the plasminogen activators and thus an important component of the coagulation system that down-regulates fibrinolysis. Reduced PAI-1 levels result in increased fibrinolysis and an associated bleeding diathesis. The other PAI, plasminogen activator inhibitor-2 (PAI-2), is secreted by the placenta and only present in significant amounts during pregnancy. Test kits for murine PAI-1 are available commercially: thus, free, latent or complex PAI-1 present in plasma reacts with the capture antibody coated and dried on a microtiter plate. Any unbound PAI-1 is washed away and an anti-PAI-1 primary antibody is added. Excess primary antibody is washed away and bound antibody, which is proportional to the total PAI-1 present in the samples, is then reacted with the secondary antibody. Following an additional washing step, TMB is then used for color development at 450 nm. The amount of color development is directly proportional to the concentration of total PAI-1 in the sample. A baseline level for PAI-1 can be established that reflects the levels in a healthy individual. A healthy individual should have lower levels of PAI-1 than a diseased individual. If levels are detected with the biomarker panel that are above the baseline level, it can be determined that the individual has vascular disease or is at risk of developing vascular disease. Other levels can determine the stage or progression of vascular disease.

The biomarker panel can alternatively include a three-panel test for endothelial glycocalyx integrity that detects syndecan-1 (SDC1), heparan sulfate (HS), and hyaluronidase (HAD).

Syndecans are transmembrane domain proteins that carry three to five heparan sulfate and chondroitin sulfate chains, which harbor a variety of important ligands including fibroblast growth factors, vascular endothelial growth factor, transforming growth factor-beta, fibronectin, and antithrombin-1. Syndecan-1 (SDC1) is a cell surface heparan sulfate proteoglycan, which is an important component of the protective endothelial glycocalyx lining the luminal surface of blood vessels. Key roles for SDC1 is in endothelial mechano-sensing and regulation of endothelial integrity and function. Shedding of syndecan-1 and heparan sulfate into the circulation is associated with inflammatory disease and atherosclerosis. Test kits for syndecan, for example test kit precoated with monoclonal antibody specific to SDC1 are available commercially. Thus, samples are then added to the appropriate microtiter plate wells with a biotin-conjugated polyclonal antibody preparation specific for SDC1. Next, Avidin conjugated to Horseradish Peroxidase (HRP) is added to each microplate well and incubated. Then a TMB substrate solution is added to each well. Only those wells that contain SDC1, biotin-conjugated antibody and enzyme-conjugated Avidin will exhibit a change in color. The enzyme-substrate reaction is terminated by the addition of a sulphuric acid solution and the color change is measured spectrophotometrically at a wavelength of 450 nm±10 nm. The concentration of SDC1 in the samples is then determined by comparing the O.D. of the samples to the standard curve. A baseline level for SDC1 can be established that reflects the levels in a healthy individual. A healthy individual should have lower levels of SDC1 than a diseased individual. If levels are detected with the biomarker panel that are above the baseline level, it can be determined that the individual has vascular disease or is at risk of developing vascular disease. Other levels can determine the stage or progression of vascular disease.

Heparan sulfates (HSs) are highly negatively charged polysaccharides with 1→4-linked sulfated glucosamine and uronic acid repeating disaccharide units. HSs are present on the cell surface as well as in the extracellular matrix and bind to proteins involved in anticoagulation, angiogenesis, microbial infection, and monocyte adhesion. HSs are glycoproteins with the common characteristic of containing one or more covalently attached chains, including syndecans and glycosylphosphatidylinositol-anchored proteoglycans (glypicans), the secreted extracellular matrix HSPGs (agrin, perlecan, type XVIII collagen), and the secretory vesicle proteoglycan, serglycin. HSs are implicated in the pathogenesis of atherosclerosis by their ability to trap plasma lipoproteins in the arterial wall and by their influence on cellular migration, adhesion and proliferation. Intact HS chains are anti-atherogenic. ELISA test kits for heparan sulfate are available commercially. The test includes pretreatment of serum with proteinase (actinase E) to digest serum proteins. One volume of dissolved Actinase E (20 mg/mL in actinase E dissolution buffer) can be added against ten volumes of serum and then mixed. Proteins can be digested at 55° C. for 16-20 hours in a water bath. After digestion, the mixture can be boiled for 5 minutes to stop digestion. After boiling, the mixture can be brought to room temperature (15-25° C.) and then centrifuged 3,000 rpm, for 10 minutes. After centrifugation, the supernatant can be taken and mixed well. The supernatant is applied to Heparan Sulfate ELISA kit. HS values can be calculated in pretreated samples according to the Heparan Sulfate ELISA kit procedure. The calculated HS values must be multiplied dilution factors as below to determine the HS concentration in serum. HS concentration=calculated HS value×dilution factor×1.1. A baseline level for HS can be established that reflects the levels in a healthy individual. A healthy individual should have lower levels of HS than a diseased individual. If levels are detected with the biomarker panel that are above the baseline level, it can be determined that the individual has vascular disease or is at risk of developing vascular disease. Other levels can determine the stage or progression of vascular disease.

Hyaluronic acid (HA, also called hyaluronan or hyaluronate) is a negatively charged, nonsulfated large linear glycosaminoglycan (a class of negatively charged polysaccharides) of repeating disaccharide structure D-Glucuronic acid (UDP-GlcA) and N-acetylglucosamine (UDP-GlcNac), which is a principal component of endothelial glycocalyx. HA is distributed widely throughout connective, epithelial, and neural tissues. HA is the simplest glycosaminoglycan that provides compression strength, lubrication and hydration. A disturbed HA is atherogenic. The removal of HA-rich glycocalyx with hyaluronidase is associated with increased vascular permeability leading to atherogenic insults. Increased plasma HA and hyaluronidase levels are found associated with endothelial glycocalyx damage, presence of microvascular diseases and carotid intima-media thickness.

A coated well immunoenzymatic assay for the quantitative measurement of hyaluronidase (HAD) utilizes a polyclonal anti-HAD antibody and an HAD-HRP conjugate. The assay sample and buffer are incubated together with HAD-HRP conjugate in pre-coated plate for one hour. After the incubation period, the wells are decanted and washed five times. The wells are then incubated with a substrate for HRP enzyme. The product of the enzyme-substrate reaction forms a blue colored complex. Finally, a stop solution is added to stop the reaction, which will then turn the solution yellow. The intensity of color is measured spectrophotometrically at 450 nm in a microplate reader. The intensity of the color is inversely proportional to the HAD concentration since HAD from samples and HAD-HRP conjugate compete for the anti-HAD antibody binding site. Since the number of sites is limited, as more sites are occupied by HAD from the sample, fewer sites are left to bind HAD-HRP conjugate. Standards of known HAD concentrations are run concurrently with the samples being assayed and a standard curve is plotted relating the intensity of the color (O.D.) to the concentration of HAD. The HAD concentration in each sample is interpolated from this standard curve. A baseline level for HA can be established that reflects the levels in a healthy individual. A healthy individual should have lower levels of HA than a diseased individual. If levels are detected with the biomarker panel that are above the baseline level, it can be determined that the individual has vascular disease or is at risk of developing vascular disease. Other levels can determine the stage or progression of vascular disease.

The biomarker panel can also include any combination of the above-described biomarkers, i.e. they are not limited to being used in combination in just the three-panel test and four-panel test. For example, another preferred combination can include PAI-1, HS, and HAS-1 as a blood test that defines vascular leakage and clot onset to correlate with plaque formation. As shown in the examples below, these three biomarkers are highly correlative with plaque formation.

The biomarker panels can be used alone or in combination. For example, the biomarker panels can be used individually if there is a strong correlation established for any of the biomarkers in that particular panel, or the combination of biomarker panels can be used to ensure reliability.

In general, the biomarker panel can use a support structure such as a flat microwell plate (such as an ELISA plate) that has multiple wells to hold samples. Various enzymes or antibodies can be applied to the wells as needed for each test, such as those described above. A housing can enclose the biomarker panel to prevent contamination or unwanted spread of samples, in plastic or another suitable material.

The biomarker panels of the present invention can be included in a kit. The kit can include the biomarker panels (the four-panel test, the three-panel test, both the four-panel and three panel tests, or any combination of the above-described biomarkers) instructions for use, materials to take and apply samples to the panel (such as, but not limited to, swabs, syringes, or vials), and descriptions of biomarker levels and their meaning (such as normal values). The kit can include various antibodies as needed to detect the biomarkers.

The biomarker panels can be used to detect the presence of vascular disease or propensity to develop vascular disease in the following method. A sample is taken (preferably by a healthcare practitioner) and applied to the biomarker panel (either the four-panel test for clotting, the three-panel test for glycocalyx integrity, both as described above, or any combination of the above-described biomarkers). The sample reacts with various reagents in the panel based on the presence of the biomarkers described above. Preferably, the sample applied to the panel is sent to a lab for analysis. Results of the reaction can provide a colorimetric result and can be read in a colorimeter. Alternatively, any other method of detection and quantification can be used, such as, but not limited to, Western blot, immunoprecipitation, immunohistochemistry, Enzyme-linked immunosorbent assay (ELISA), Radio Immuno Assay (RIA), radioreceptor assay, proteomics methods (such as mass spectrometry), or quantitative immunostaining methods. If any or all of the biomarkers are detected, it can be determined if the individual has vascular disease or the propensity to develop vascular disease by comparing the biomarker levels to known baseline levels for healthy individuals. In other words, if levels of the biomarkers are detected that are above the baseline level, it can be determined that the individual has vascular disease or is at risk of developing vascular disease.

The biomarker panel can also be used to determine the stage of vascular disease in an individual (i.e. the progression of vascular disease in the individual). A sample is taken (preferably by a healthcare practitioner) and applied to the biomarker panel (either the four-panel test for clotting, the three-panel test for endothelial glycocalyx integrity, both as described above, or any combination of the above-described biomarkers). The sample reacts with various reagents in the panel based on the presence of the biomarkers described above. Preferably, the sample applied to the panel is sent to a lab for analysis. Results of the reaction can provide a colorimetric result and can be read in a colorimeter or by any other method described above. If any or all of the biomarkers are detected, it can be determined what stage of vascular disease the individual has by comparing the results to known stage levels. Based on the results of the stage of vascular disease, the individual can be proscribed medication that is appropriate for that particular stage.

The biomarker panels can also be used in a method of monitoring the efficacy of drugs during drug development against cardiovascular diseases or other diseases involving inflammation, disruption of blood vessels, removal of plaques, or treatment of clot formation. A sample can be taken (preferably by a healthcare practitioner) from an individual receiving a drug being tested. The sample can be applied to a biomarker panel (either the four-panel test for clotting, the three-panel test for endothelial glycocalyx integrity, both as described above, or any combination of the above-described biomarkers). The sample reacts with various reagents in the panel based on the presence of the biomarkers described above. Preferably, the sample applied to the panel is sent to a lab for analysis. Results of the reaction can provide a colorimetric result and can be read in a colorimeter or by any other method described above. If the presence of any or all of the biomarkers are detected, indicating the presence of inflammation, disruption of blood vessels, plaques, or clot formation (among any other symptoms described above), it can be determined if the drug is effective by comparing the results to known baseline levels for healthy individuals. A higher than baseline level would indicate that the drug has not been effective in treatment.

The biomarkers included in the panels of the present invention measure factors produced early on in the clot formation process. Therefore, each of these biomarkers alone are significant as well as together in the panels in predicting the initiation of the biologic process (oxidation and immunogenic and/or inflammatory process) that leads to the formation of the clots. Also, the "lipid panel" devised by the American Heart Association is not predictive of cardiovascular disease: they measure cholesterol and triglycerides. Therefore, the biomarker panel of the present invention can replace this lipid panel for routine diagnostics.

The biomarker panel can also be used in a method of monitoring the progress of various vascular disease treatments. A sample is taken from an individual currently receiving treatment for vascular disease and applied to the biomarker panel (either the four-panel test for clotting, the three-panel test for endothelial glycocalyx integrity, or both as described above). The sample reacts with various reagents in the panel based on the presence of the biomarkers described above. Results can be read by any method described above. Based on the detection of any or all of the biomarkers by comparing the results to a predetermined baseline, it can be determined if the treatments are working to reverse or prevent vascular disease. The treatments that can be monitored include, but are not limited to, anti-inflammatories (such as non-steroidal anti-inflammatory drugs (NSAIDS), steroids, or immune selective anti-inflammatory derivatives (ImSAIDs)), anticoagulants (such as alteplase, ardeparin, dalteparin, danaparoid, enoxaparin, fondaparinux, lepirudin, urokinase, or warfarin), antioxidants (such as glutathione, alpha-lipoic acid, CoQ10, resveratrol, carotenoids, astaxanthin Vitamin C, or Vitamin E), supplements, and any other suitable therapeutics.

Detecting various biomarkers used in the biomarker panels of the present invention is shown in EXAMPLE 1 below.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Materials and Methods

Mice

For the pilot study, 48 ten week old male C57/Bl6 mice were obtained from Jackson Laboratories. Three mice were raised from 6 weeks on a regular diet and served as controls, and the remaining 45 were raised on a 60% fat diet (D12451, DIO series diet, Opensource Diets). For the bacterial dosage test, 16 ten week old male C57/Bl6 mice were divided into 4 treatment groups and maintained on a normal diet.

Treatments 3,3',4,4'-Tetrachlorobiphenyl (PCB-77) was obtained from Neosyn Laboratories. 100 mg of the dry chemical was suspended in 15.22 ml of corn oil to deliver 150 µmol/kg in 0.2 ml per mouse. *Porphyromonas gingivalis* 381 (ATCC 33277) was obtained from ATCC. The bacteria were stored frozen prior to use. The bacteria were cultured in multiple sterile tubes in 40 ml of supplemented tryptic soy broth at 37° C. under anaerobic conditions. The cultures were centrifuged, the medium removed, and the samples combined. A 100 µl sample of the bacteria was mixed with 100 µl of medium, and added to a 96 well plate. A microplate reader was used to measure the optical density at 600 nm to determine the concentration of bacteria. Based on the bacterial concentration, the samples were diluted to appropriate concentration with 2% carboxymethylcellulose in sterile phosphate buffered saline (PBS).

Gavage

A 20 gauge curved feeding needle was used to administer 0.2 ml of the treatment into the stomach of each mouse.

Light Isoflurane gas anesthesia was utilized to facilitate introduction of the needle to the esophagus, and to decrease the risk of animal injury due to movement during gavage.

ELISA

Six test kits were used to analyze the collected plasma samples: Thrombin-Anti-Thrombin Complex ELISA (Kamiya Biomedical Company, Thousand Oaks, Calif.), Anti-Thrombin III ELISA (ABCam), Total Plasminogen Activation Inhibitor-1 ELISA (Molecular-Innovive), Syndecan-1 ELISA (USCN, Houston, Tex.), and Heparan Sulfate ELISA and Hyaluronan Synthase 1 ELISA (antibodies-online). All tests were performed on plasma, diluted to the fall within the standard curve if necessary, and carried out according to the manufacturer's instructions.

Methods

The gavage schedule was carried out as listed in FIG. 1A. Sufficient bacteria were unable to be grown to produce the suggested dosage of $3\times10^{11}$ bacteria per mouse, which is much higher than the dosages used in the scientific literature, so the dosage was decreased to $5\times10^9$. There were 3 deaths overnight following the first bacterial gavage, so the second bacterial gavage was delayed to day 6, and reduced to $1.5\times10^9$.

For the dosing test, the mice received a gavage of bacteria on day 1 and day 6, to simulate the gavage schedule employed in the pilot study. FIG. 1B lists the bacterial dosages.

Sacrifice and Harvest

The mice were sacrificed on days 10, 15, or 20 according to the experimental plan (three each from groups 1-5). The animals were anesthetized by intraperitoneal injection of 90 mg/kg Ketamine and 8 mg/kg Xylazine, and Isoflurane gas anesthesia. Blood was collected by retro-orbital bleeding or from the heart and mixed with 50 mg/ml heparin to prevent clotting. The thorax was opened to expose the heart, and saline was injected into the left ventricle, with the right atrium opened to allow the drainage of blood and saline. The heart was perfused with at least 5 ml of saline and until no blood was observed in the drainage from the atrium. The heart was carefully dissected and frozen for histological sectioning. Plasma was collected from the blood samples by centrifuging at 1000 rpm for 15 minutes, and collecting the supernatant. The samples were stored at $-80°$ C. until analysis.

Histology

The hearts were prepared as frozen sections. They were mounted in blocks and 10 µm thick sections were cut through the aortic valve, with 30 sections per mouse. Oil Red O staining was used to visualize the lipid content of the plaques. Multiple 10 µm sections at the level of the aortic sinus were analyzed for the presence of oil Red O lipid staining, plaque size, amount of fibrous tissue, and inflammation. The percentage of the lumen occupied by the first three features was calculated using Image Pro Plus. The average percentage of each feature was used to score the three features with the following scale: For fibrous tissue, lipid staining, and plaque size: $0=<2\%$, $1=\geq2\%$, $2=\geq4\%$, $3=\geq6\%$, $4=\geq10\%$. The level of inflammation in each section was scored on the following scale: 0=no inflammatory cells observed, 1=few macrophages with no giant cells, 2=foam cells present, 3=foam cells with cholesterol, 4=foam cells, giant cells, and cholesterol present. The inflammation score was averaged over all the sections, then converted to an overall score: For inflammation: $0=<0.2$, $1=\geq0.2$, $2=\geq0.4$, $3=4=\geq1$.

Results

Pathology

Figure 2B:

No inflammation or plaques were found in Groups 1, 2, 5 and 6; however, inflammatory cells as indicated by general lipid staining throughout Group 3 (FIG. 2A) and well-defined atherosclerotic plaque in Group 4 (FIG. 2B).

Correlation of biomarkers with plaque formation or vascular inflammation:

Blood was drawn from the animals at various intervals and analyzed for biomarkers. Of the different markers evaluated, three showed significant levels in groups 3 and 4 animals (particularly in day 15 and 20), indicating high correlations to inflammation or plaque formation (statistically analyzed by independent T-test). These biomarkers include plasminogen activator inhibitor-1 (PAI-1), heparan sulfate, and hyaluronan synthase; syndecan-1 is a marginally predictive biomarker.

A. Highly Correlative Biomarkers

Figure 3:
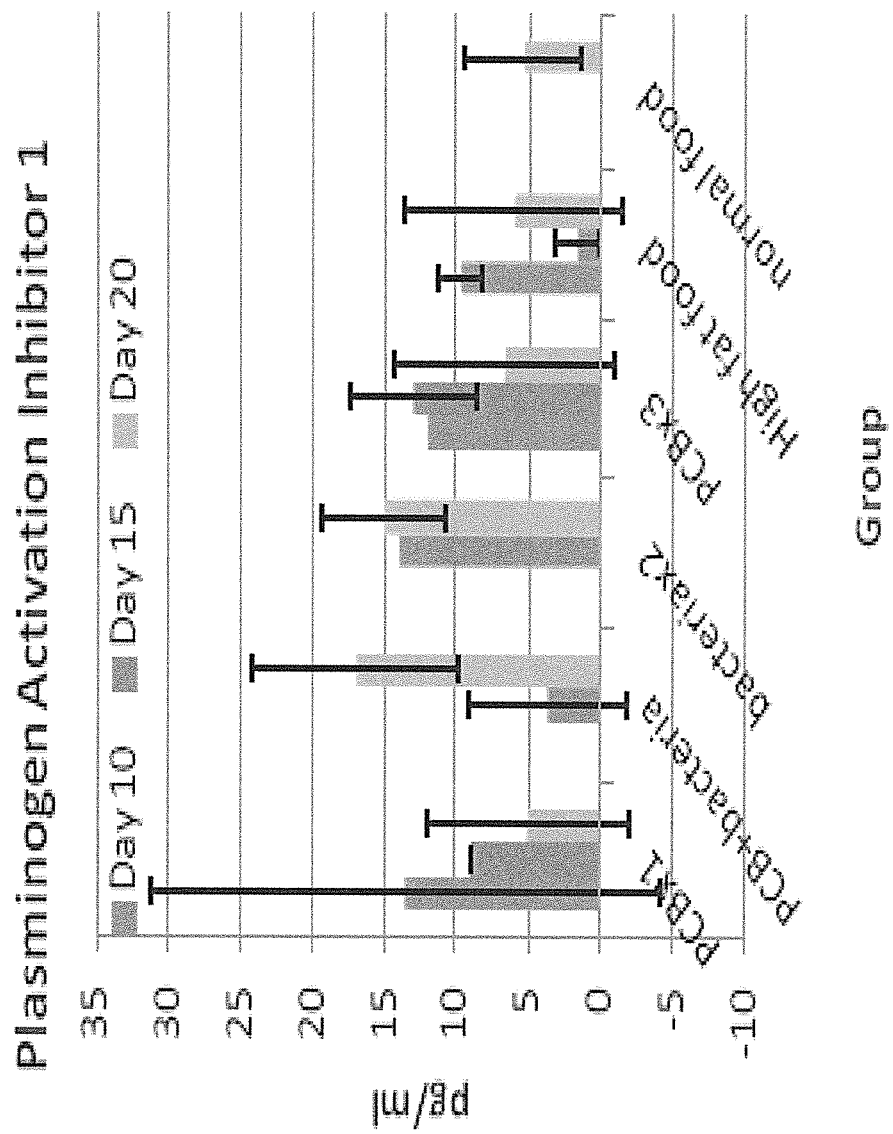
FIG. 3 is a graph of total plasminogen activation inhibitor-1 levels.

1. Plasminogen Activator Inhibitor-1 (PAI-1):

FIG. 3 shows that PAI-1 was significantly elevated in the 20 day sacrifice than control (group 6: normal food).

2. Heparan Sulfate (HS)

Figure 4:
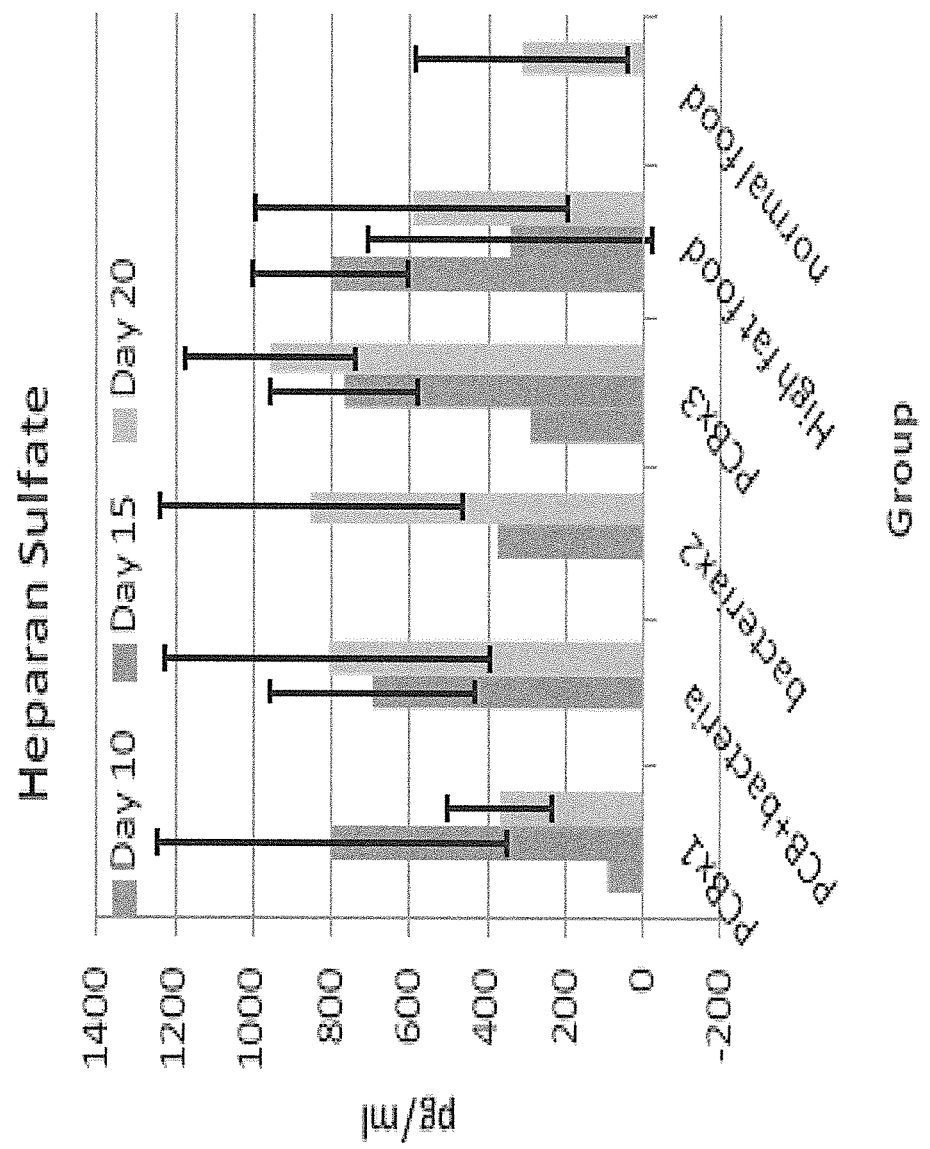
FIG. 4 is a graph of heparan sulfate levels.

FIG. 4 shows that HS levels at 20 day sacrifice were significantly higher than in the control group.

3. Hyaluronan Synthase 1 (HAS-1)

Figure 5:
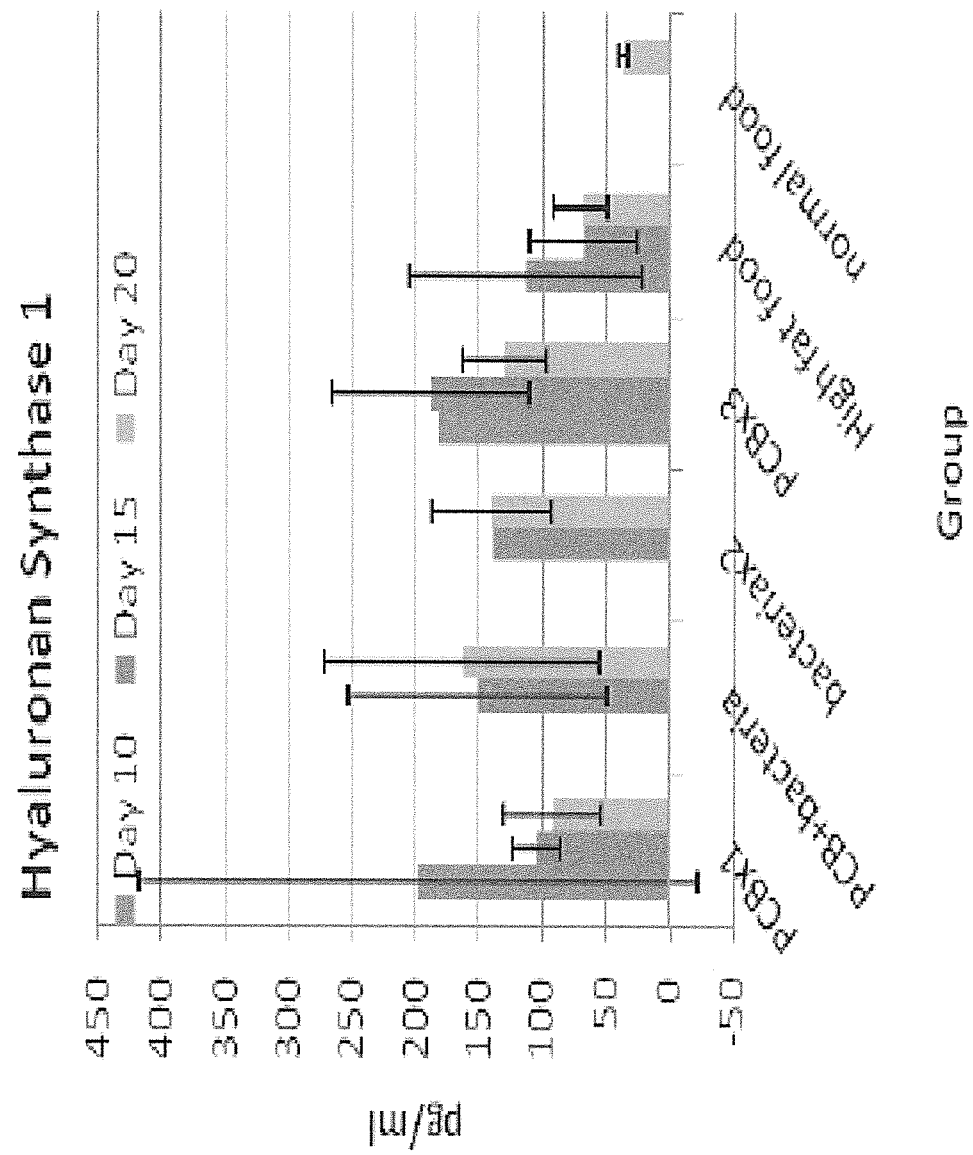
FIG. 5 is a graph of hyaluronan synthase 1 levels.

FIG. 5 shows that hyaluronan synthase at 20 day sacrifice was significantly higher than the same time point in the control group.

B. Marginal Biomarker

1 Syndecan-1

Figure 6:
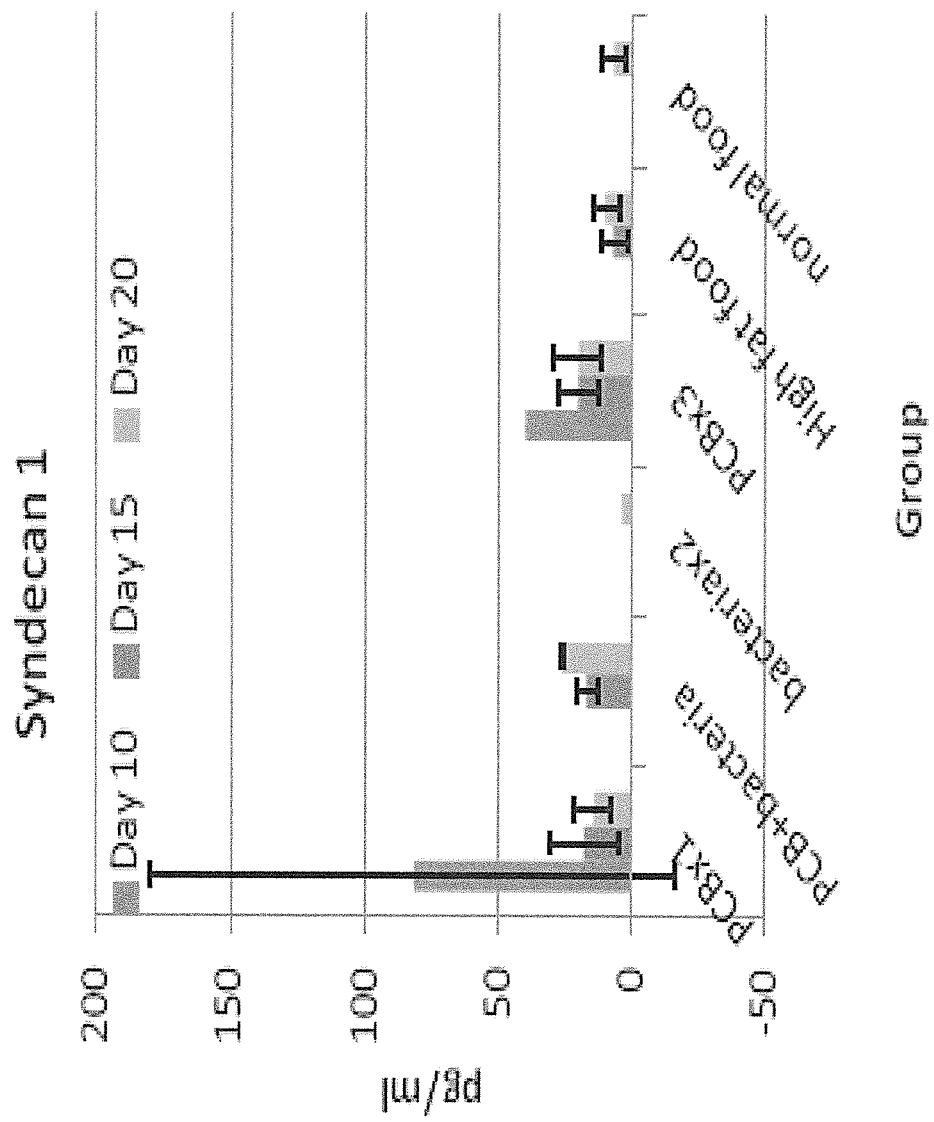
FIG. 6 is a graph of syndecan-1 levels.

FIG. 6 shows that syndecan-1 at 10 days was significantly higher than the same time point in the control group.

C. Poorly prognostic of inflammation or plaque formation:

1 Thrombin-Anti-Thrombin (TAT)

Figure 7:
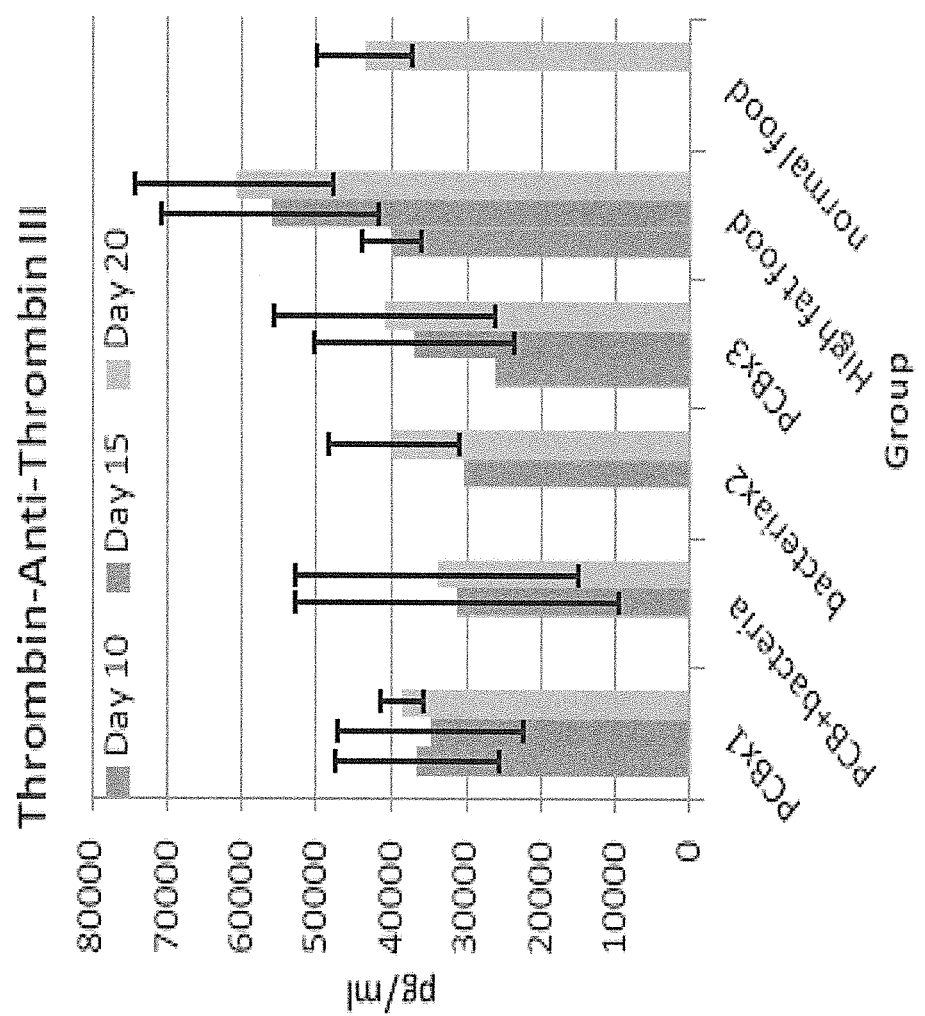
FIG. 7 is a graph of thrombin-anti-thrombin III levels.

As shown in FIG. 7, no correlations were observed with the TAT complexes.

2. Antithrombin III

Figure 8:
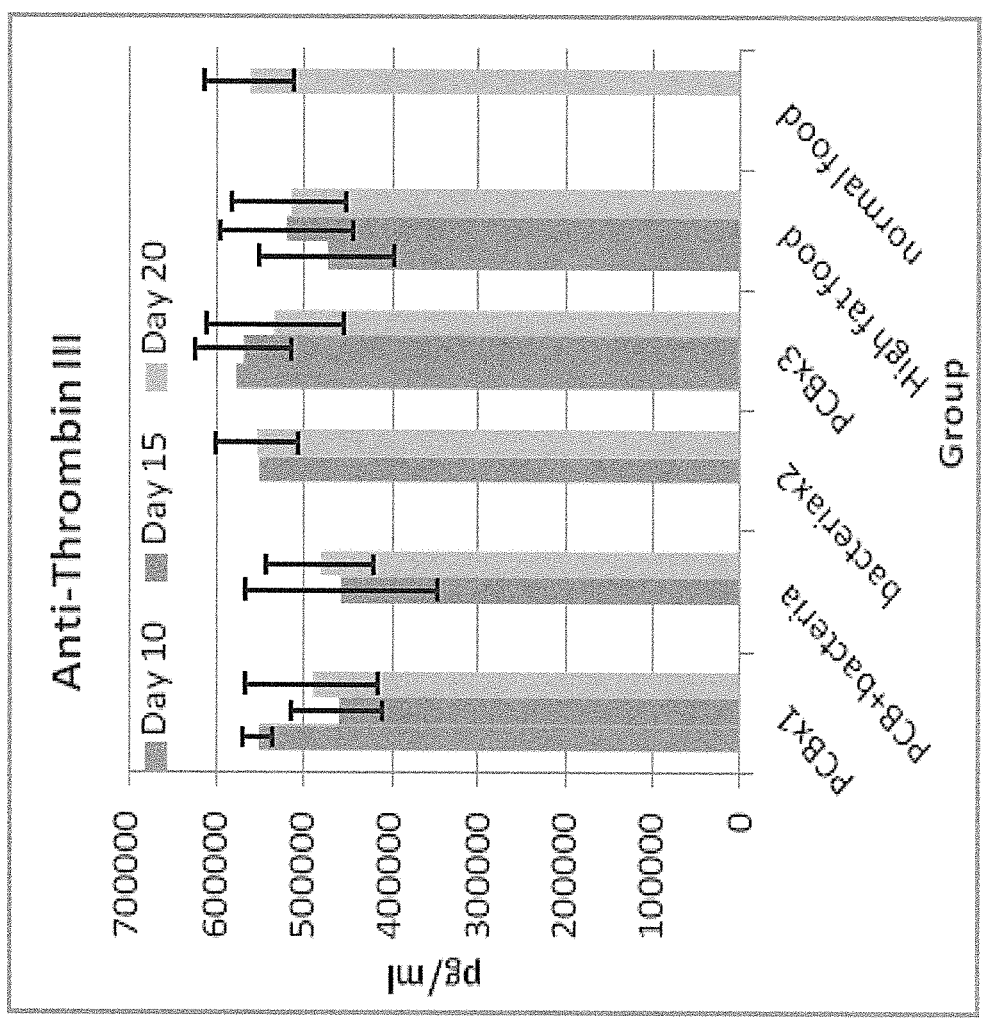
FIG. 8 is a graph of anti-thrombin levels.

As shown in FIG. 8, there was no significant difference in the levels of Anti-Thrombin III between the treatment groups at any time point, or between time points within the groups, as measured by independent T-test.

Summary

Figure 9:
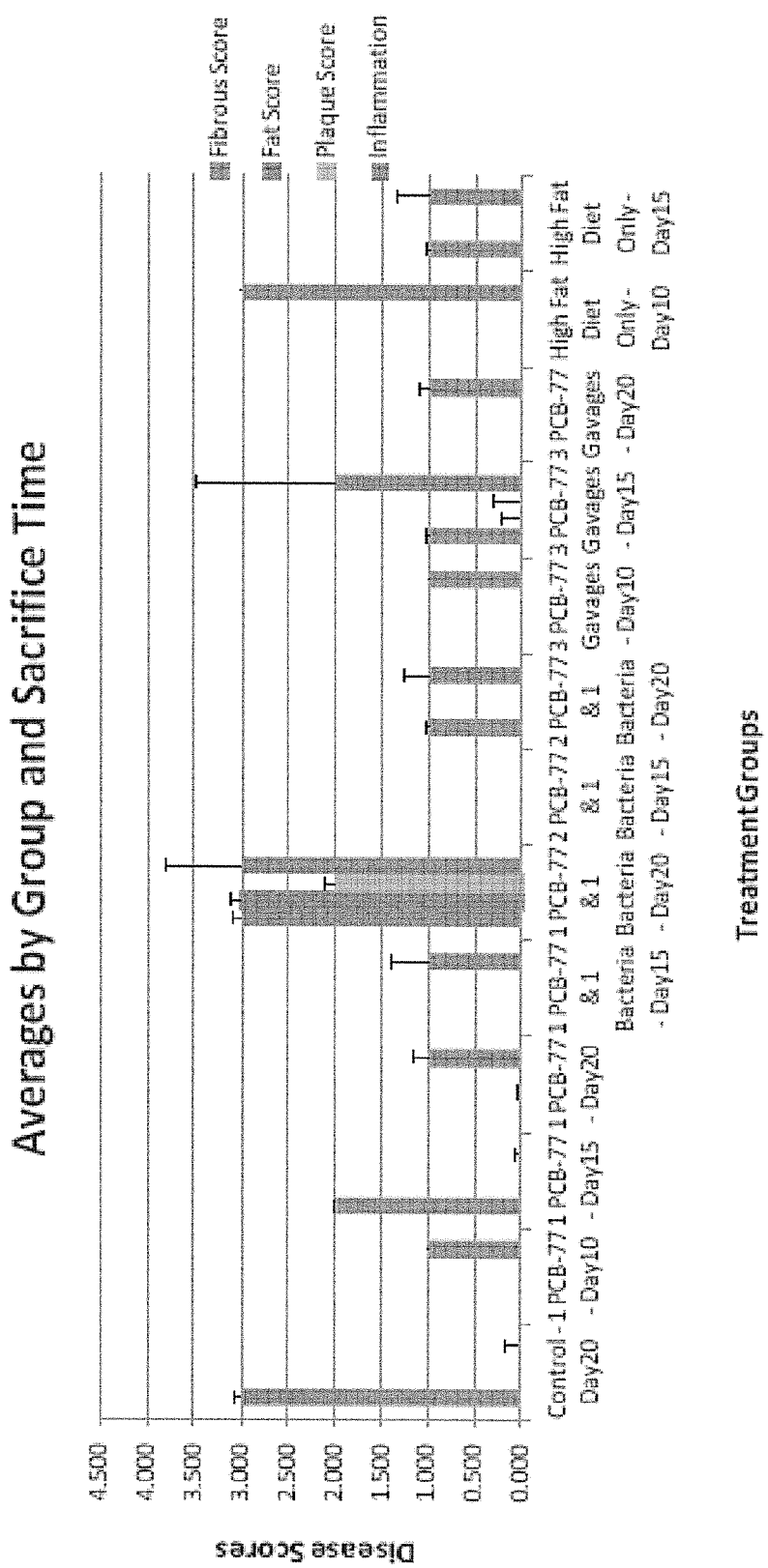
FIG. 9 is a graph of average disease scores for treatment groups and sacrifice times.

FIG. 9 shows graphically the average scores for each group and time point, indicating PCB77 treatment as the most significant risk factor to producing inflammation and plaque.

EXAMPLE 2

Materials and Methods

A novel model of atherosclerosis in mice was developed, using a high fat diet and administration of a polychlorinated biphenyl (3,3',4,4'-Tetrachlorobiphenyl; PCB-77) that promotes both obesity and atherosclerosis and the additional oral administration of a bacteria responsible for tooth decay, *Porphyromonas gingivalis* 381 (ATCC 33277). The objective of this study was to examine the association of biomarkers with the murine model of atherosclerosis in mice treated with a strategy to protect and repair endothelial glycocalyx. Eighty-four (84) ten week old male C57/Bl6 mice were obtained from Jackson Laboratories. Thirty-two mice were raised from 6 weeks on a regular diet and served as controls, and the remaining mice were raised on a 60% fat diet (D12451, DIO series diet, Opensource Diets). 3,3',4,4'-Tetrachlorobiphenyl (PCB-77) was obtained from Neosyn Laboratories. The dry chemical was suspended in 15.22 ml of corn oil to deliver 200 μmol/kg in 0.2 ml by gavage per mouse.

ELISA

Four test kits were used to analyze the collected plasma samples: Heparan Sulfate ELISA and Hyaluronan Synthase 1 (HAS-1) ELISA (Antibodies-Online), Total Plasminogen Activation Inhibitor-1 (PAI-1) ELISA (Molecular-Innovive) and Syndecan-1 (SDC1) ELISA (USCN, Houston, Tex.). All tests were performed on plasma, diluted to the fall within the standard curve if necessary, and carried out according to the manufacturer's instructions.

Sacrifice and Harvest

The mice were sacrificed on days 4, 11, or 18 according to the experimental plan (three each from groups). The animals were anesthetized by intraperitoneal injection of 90 mg/kg Ketamine and 8 mg/kg Xylazine, and Isoflurane gas anesthesia. Blood was collected by retro-orbital bleeding or from the heart and mixed with 50 mg/ml heparin to prevent clotting. The thorax was opened to expose the heart, and saline was injected into the left ventricle, with the right atrium opened to allow the drainage of blood and saline. The heart was perfused with at least 5 ml of saline and until no blood was observed in the drainage from the atrium. The heart was carefully dissected and frozen for histological sectioning. Plasma was collected from the blood samples by centrifuging at 1000 rpm for 15 minutes, and collecting the supernatant. The samples were stored at −80° C. until analysis.

Results

Hyaluronan Synthase 1 (HAS-1)

Figure 10:
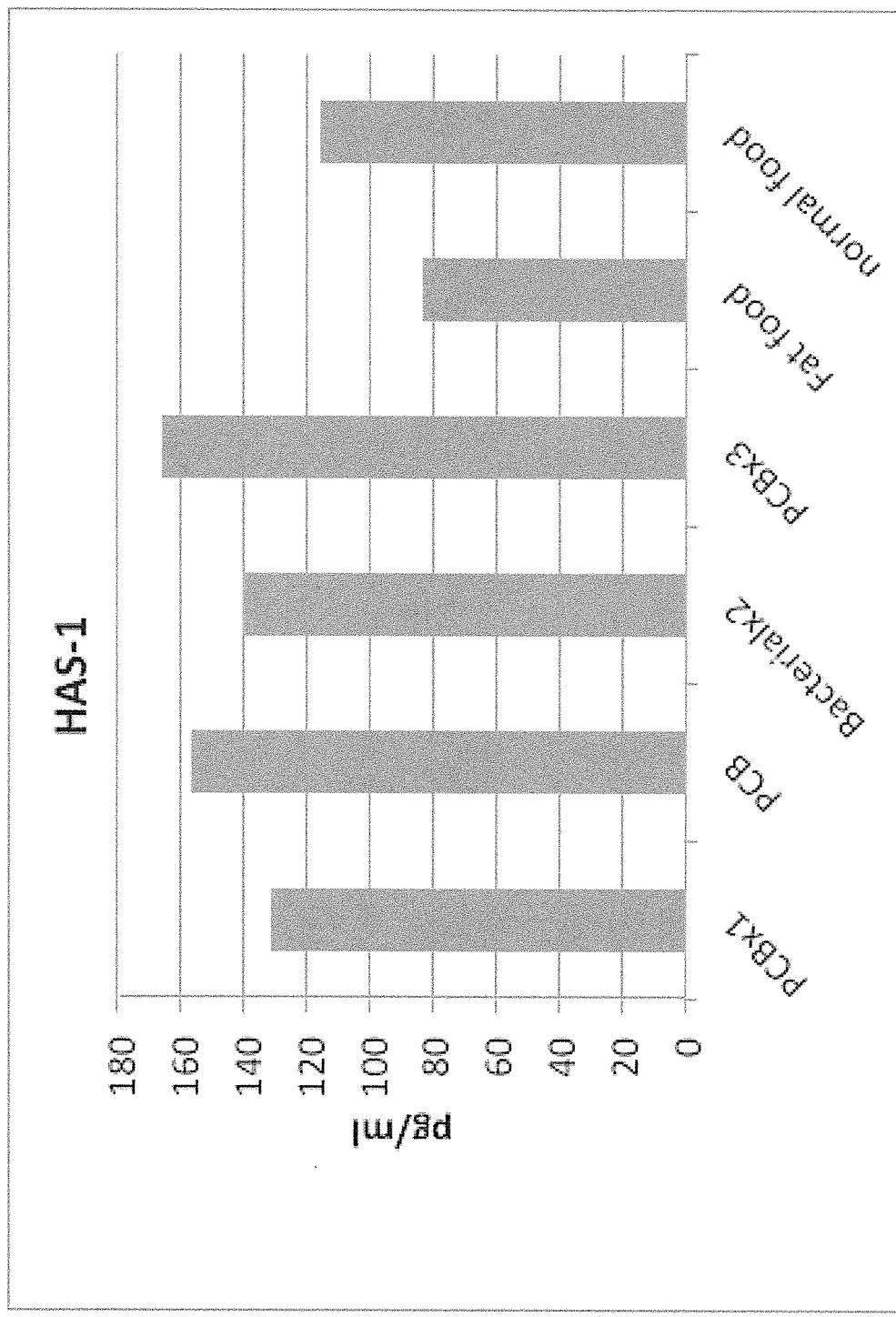
FIG. 10 is a graph of hyaluronan synthase levels.

FIG. 10 shows the results for Hyaluronan Synthase 1 (HAS-1). It was observed that the highest HAS-1 levels occurred in the mice on the high fat diet treated with PCB on Day 1 and 3 and sacrificed at Day 4. Reductions in HAS-1 levels have been observed in mice treated to with compounds designed to restore and repair the endothelial glycocalyx.

Heparan Sulfate (HS)

Figure 11:
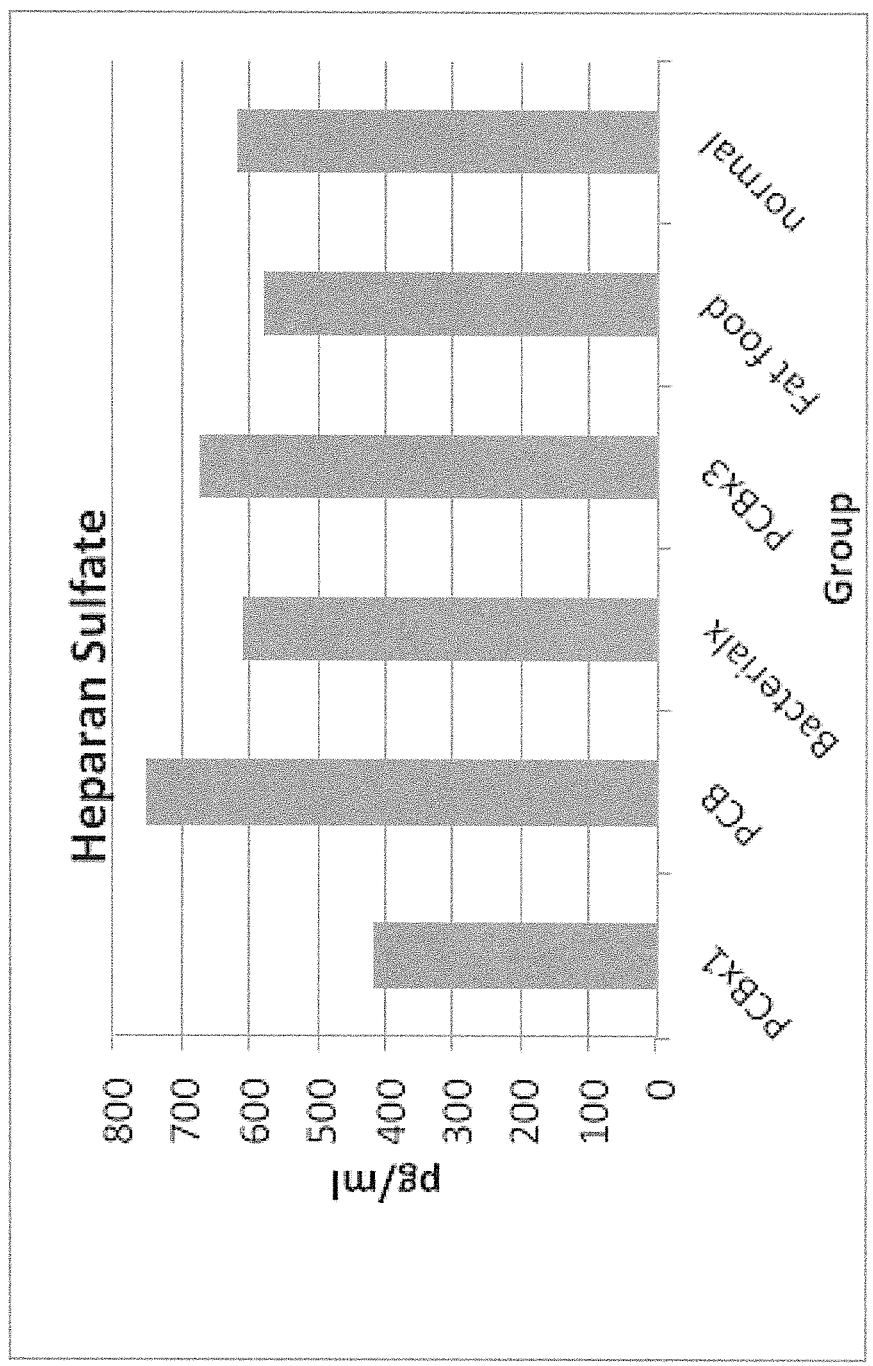
FIG. 11 is a graph of heparan sulfate levels.

FIG. 11 shows the results for Heparan Sulfate. An elevation in HS was observed in mice treated PCB-77 and *Porphyromonas gingivalis*.

Total Plasminogen Activation Inhibitor-1 (PAI-1)

Figure 12:
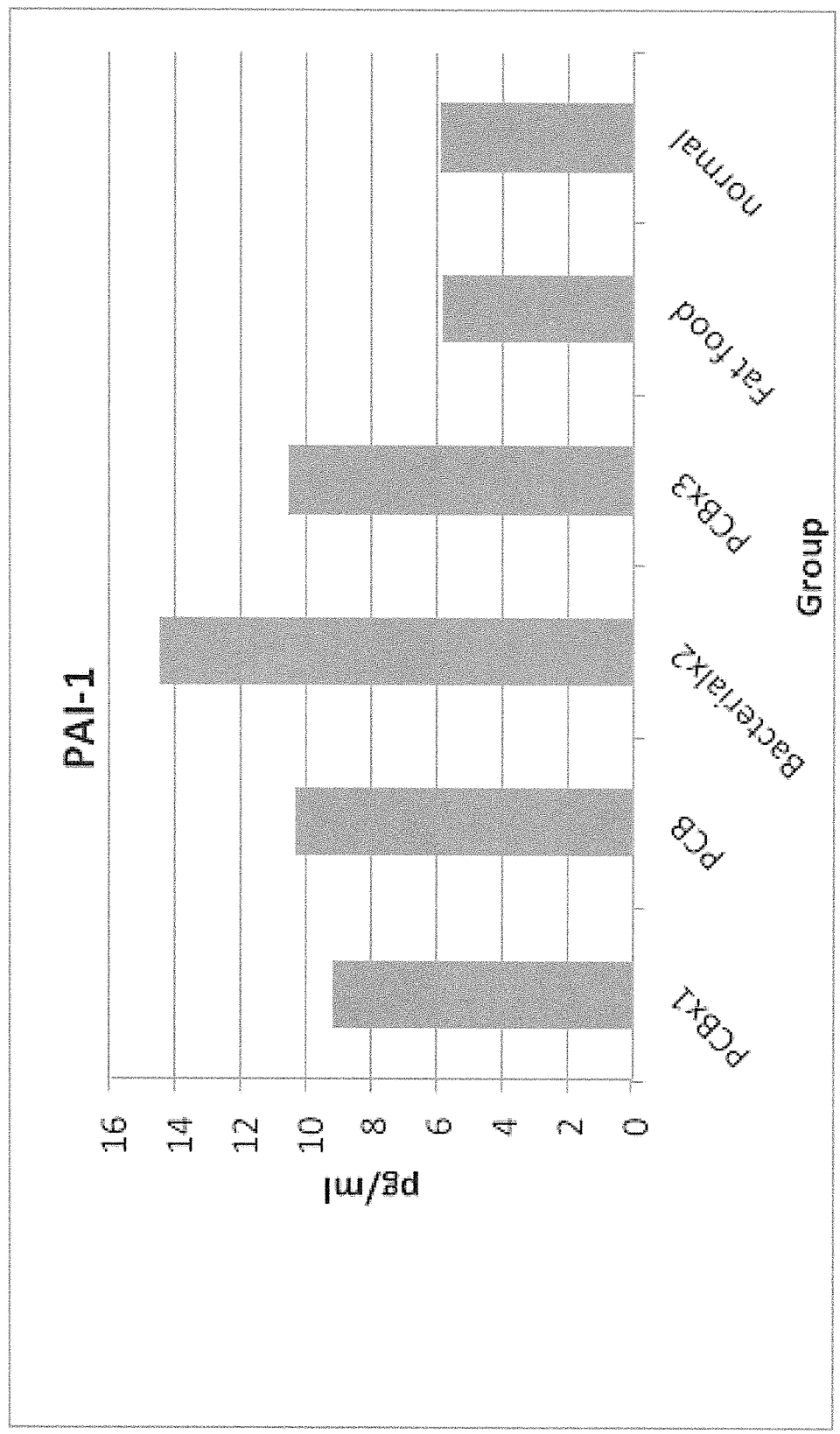
FIG. 12 is a graph of total plasminogen activation inhibitor-1 levels.

FIG. 12 shows the results for PAI-1. It was observed that high PAI-1 levels occurred in all mice treated with an insult designed to provoke an atherosclerosis response.

Syndecan-1 (SDC1)

Figure 13:
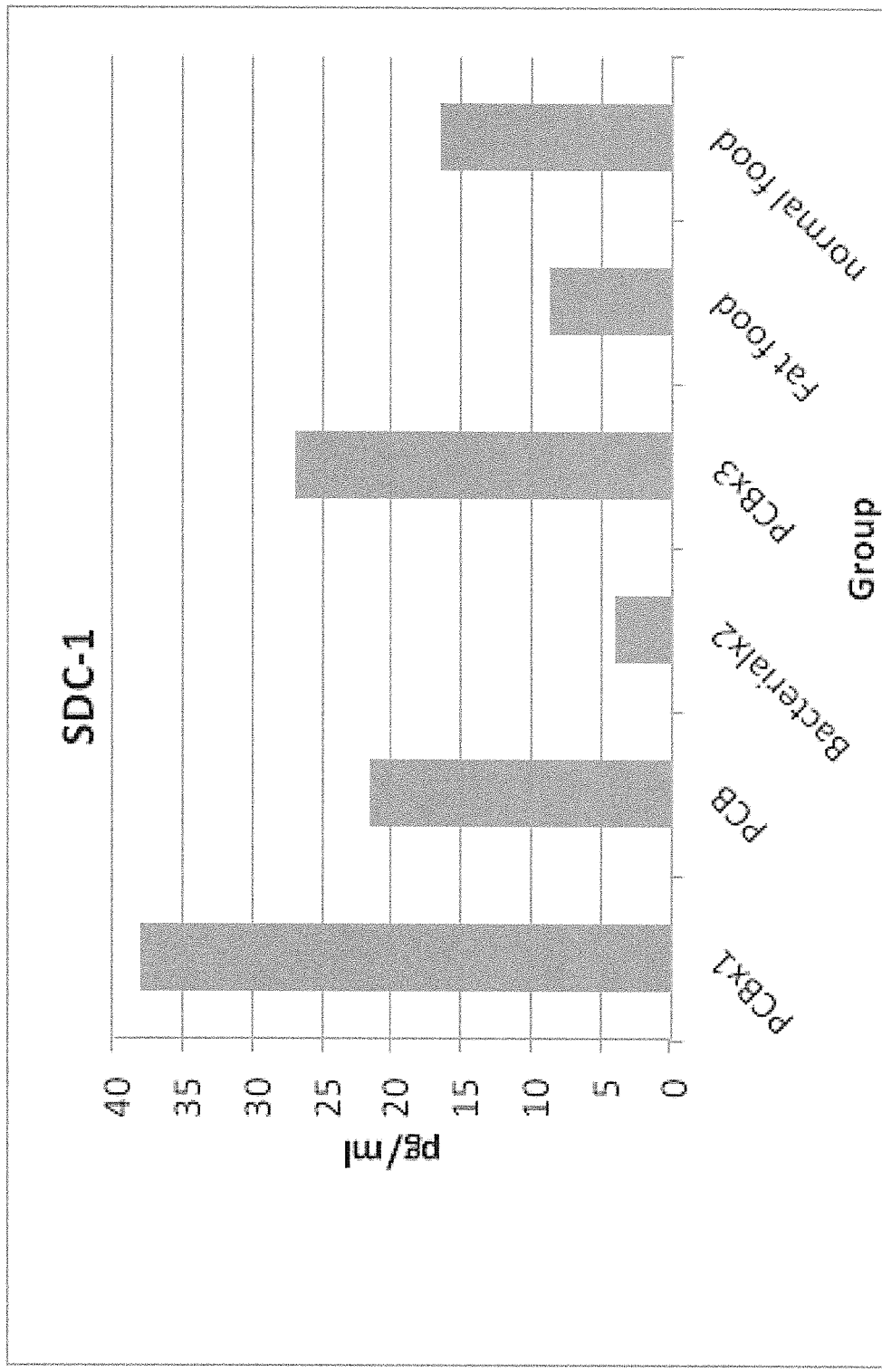
FIG. 13 is a graph of syndecan-1 levels.

FIG. 13 shows the results for SDC1. An elevation in SDC-1 was observed in mice treated PCB-77 and *Porphyromonas gingivalis*, although a high degree of variability was seen in the results for this assay.

Pathology

Figure 14A:
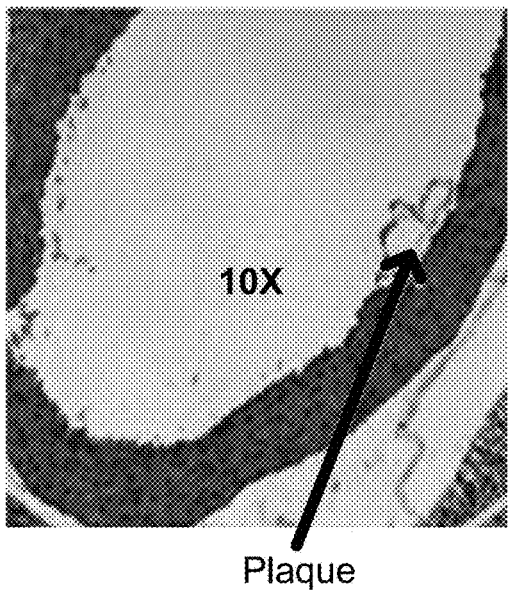
FIG. 14A is a photograph of plaque at 10×.
Figure 14B:
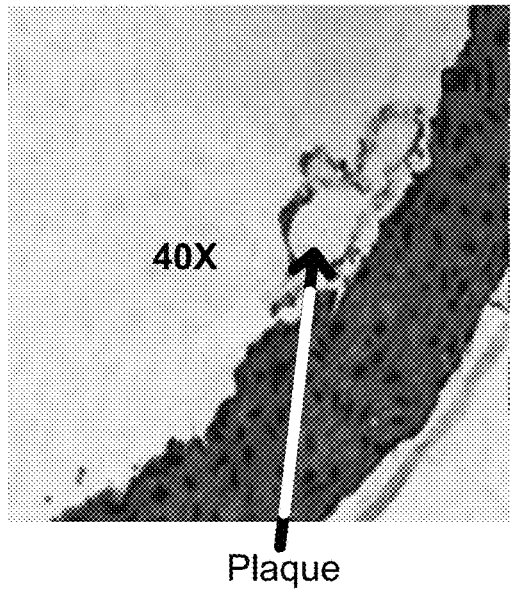
FIG. 14B is a photograph of plaque at 40×.
Figure 14C:
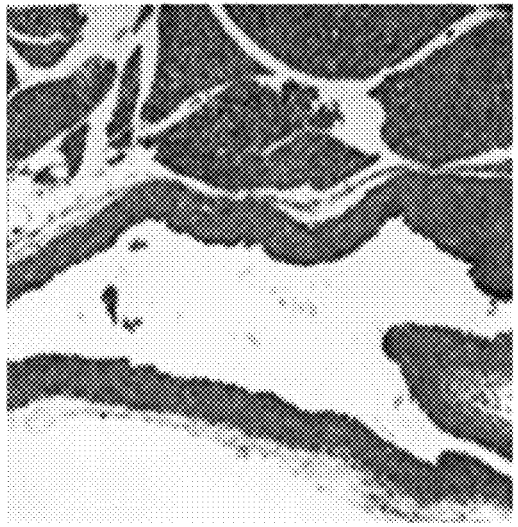
FIG. 14C is a photograph of a normal arterial wall.

The positive control group (High fat diet, PCB) revealed presence of a pathology consistent with plaque (FIGS. 14A, 10×; and 14B, 40×); fibrous material loosely attached to the surface of the arterial wall was observed in this sample. In contrast, the negative control group (Normal diet, no PCB, no treatment) exhibited the typical features of a normal arterial wall (14C).

Conclusion

The three biomarkers that were found highly correlative to plaque production are Hyaluronan Synthase (HAS-1), Heparan Sulfate (HS), and Plasminogen Activation Inhibitor-1 (PAI-1). The biochemical changes that define cardiovascular disease (CVD) are difficult to quantitate. In this regard, simplified and predictive biomarkers were developed involving blood samples to monitor onset of cardiovascular disease and its progression. These biomarkers are developed to provide a reliable predictor of cardiovascular events.

Significant smaller endothelial glycocalyx dimensions and amounts for two of its major constituents heparan sulfate and hyaluronan at the atherogenic sinus region of the carotid artery bifurcation compared with the common carotid region; perturbed endothelial glycocalyx content at pre-lesion areas within the arterial vascular tree contributes to local loss of EC barrier properties. A possible role of the endothelial glycocalyx in control of vascular wall permeability emerged, as suggested from increased local intima-to-media ratio at sites of reduced endothelial glycocalyx dimension at atherogenic risk areas. These early changes in local intima-to-media ratio were without evidence of blood cell or monocyte accumulation within the extended intimal layer, indicating a minimal inflammatory response at this very early stage.

In conclusion, predisposed arterial vascular regions have lower amounts of carbohydrate structures such as heparin sulfate and hyaluronan present within their luminal surface endothelial glycocalyx that results in locally reduced permeability barrier properties. In the present study, we reveal the endothelial cell glycocalyx as a complex 3D matrix, vulnerable to atherogenic risk factors, which, through pre-existing differences in local architecture, results locally predisposed vulnerable arterial sites A reasonable number of compounds tested exhibited an influence upon the biomarkers in the murine model of atherosclerosis, with marker changes in Hyaluronan Synthase 1 (HAS-1) and Total Plasminogen Activation Inhibitor-1 (PAI-1) in the curative model and Heparan Sulfate (HS) and Total Plasminogen Activation Inhibitor-1 (PAI-1) in the preventative protocol.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of assaying a biological sample, the method comprising:
    assaying the biological sample for a biomarker panel comprising the biomarkers hyaluronan synthase-1, plasminogen activator inhibitor (PAI-1), and heparan sulfate (HS), and combinations thereof.

2. The method of claim 1, wherein the biomarker panel additionally comprises the biomarker syndecan-1 (SDC1).

3. The method of claim 1, wherein the sample is from an individual receiving treatment for cardiovascular disease.

4. The method of claim 3, wherein the treatment is selected from the group consisting of anti-inflammatories, steroids, or immune selective anti-inflammatory derivatives, anticoagulants, antioxidants, and supplements.

5. The method of claim 1, wherein the sample is from an individual receiving a drug being tested.

6. The method of claim 1, wherein said assaying comprises using reagents for detecting the biomarkers.

7. The method of claim 6, wherein the reagents comprise antibodies for detecting the biomarkers.

8. The method of claim 7, wherein the antibodies are labeled or are capable of becoming labeled during an immunoassay.

9. The method of claim 1, wherein the sample is from an individual suspected of having, or known to have, a perturbation of the glycocalyx.

10. The method of claim 9, wherein the pertubation of the glycocalyx comprises a cardiovascular disease.

11. The method of claim 10, wherein the cardiovascular disease comprises plaque formation or vascular inflammation.

12. The method of claim 3, wherein the cardiovascular disease comprises plaque formation or vascular inflammation.

13. The method of claim 1, wherein the sample is from an individual, and the method additionally comprises treating the individual for a perturbation of the glycocalyx based on the results of the biomarker panel assay.

14. The method of claim 13, wherein the pertubation of the glycocalyx comprises a cardiovascular disease.

15. The method of claim 14, wherein the cardiovascular disease comprises plaque formation or vascular inflammation.

16. A method of treating a perturbation of the glycocalyx, wherein the method comprises treating an individual selected for treatment of the glycocalyx, wherein the individual is selected based on the results of a biomarker panel assay previously carried out according to the method of claim 8, wherein the method comprises treating the individual with an an agent selected from the group consisting of an anticoagulant, an antiplatelet agent, an anti-inflammatory agent, a steroid, an immune selective anti-inflammatory derivative, and an antioxidant or a combination thereof.

17. The method of claim 16, wherein pertubation of the glycocalyx comprises a cardiovascular disease.

18. The method of claim 17, wherein the cardiovascular disease comprises plaque formation or vascular inflammation.

19. The method of claim 1, wherein the biomarker panel additionally comprises one or more of the biomarkers soluble fibrin, thrombin-antithrombin complex, antithrombin III, and hyaluronidase.

20. The method of claim 16, wherein the biomarker panel additionally comprises the biomarker syndecan-1 (SDC1).

21. The method of claim 20, wherein the biomarker panel additionally comprises one or more of the biomarkers soluble fibrin, thrombin-antithrombin complex, antithrombin III, and hyaluronidase.

* * * * *